(12) United States Patent
Martin et al.

(10) Patent No.: US 7,410,645 B2
(45) Date of Patent: Aug. 12, 2008

(54) MORAXELLA (BRANHAMELLA) CATARRHALIS ANTIGENS

(75) Inventors: Denis Martin, St-Augustin-de-Desmaures (CA); Josée Hamel, Sillery (CA); Bernard R. Brodeur, Sillery (CA); Stéphane Rioux, Beauport (CA); Julie Couture, St-Augustin-de-Desmaures (CA)

(73) Assignee: ID Biomedical Corporation, Laval (CA)

( * ) Notice: Subject to any disclaimer, the term of this patent is extended or adjusted under 35 U.S.C. 154(b) by 380 days.

(21) Appl. No.: 10/477,592

(22) PCT Filed: May 15, 2002

(86) PCT No.: PCT/CA02/00706

§ 371 (c)(1),
(2), (4) Date: Jun. 2, 2004

(87) PCT Pub. No.: WO02/092625

PCT Pub. Date: Nov. 21, 2002

(65) Prior Publication Data

US 2004/0236087 A1    Nov. 25, 2004

Related U.S. Application Data

(60) Provisional application No. 60/290,653, filed on May 15, 2001.

(51) Int. Cl.
| | | |
|---|---|---|
| A61K 39/02 | (2006.01) | |
| A61K 39/00 | (2006.01) | |
| A61K 38/00 | (2006.01) | |
| C07H 21/04 | (2006.01) | |
| C07K 14/00 | (2006.01) | |
| C12P 21/04 | (2006.01) | |

(52) U.S. Cl. ............... 424/234.1; 424/184.1; 435/69.7; 530/350; 530/300; 536/23.7; 514/2

(58) Field of Classification Search ............... 424/178.1, 424/164.1, 234.1, 184.1; 530/23.7, 350, 530/300; 435/69.7; 514/2; 536/69.7
See application file for complete search history.

(56) References Cited

U.S. PATENT DOCUMENTS

| 6,063,386 A | 5/2000 | Dale et al. |
| 6,419,932 B1 | 7/2002 | Dale |
| 6,673,910 B1 * | 1/2004 | Breton ................... 536/23.1 |
| 6,716,433 B1 | 4/2004 | Dale |

FOREIGN PATENT DOCUMENTS

| CA | WO0218595-A2. * | 7/2002 |
| WO | 99/58563 A2 | 11/1999 |
| WO | 00/09694 A1 | 2/2000 |
| WO | 00/71724 A2 | 11/2000 |
| WO | WO 0078968 | 12/2000 |
| WO | WO 0119996 | 3/2001 |
| WO | 02/062378 A2 | 8/2002 |

OTHER PUBLICATIONS

Greenspan et al (Nature Biotechnology, 1999, 7:936-937).*
Holmes (Exp. Opin.Invest. Drugs, 2001, 10(3):511-519).*
Roitt et al (Immunology, 1993, Mosby, St. Louis, p. 7.7-7.8).*
Herbert et al (The Dictionary of Immunology, Academic Press, 3rd Edition, London, 1985, pp. 58-59).*
Bowie et al (Science, 1990, 257:1306-1310).*
Gentry-Weeks et al., "Cloning and Sequencing of a Gene Encoding a 21-Kilodalton Outer Membrane Protein from *Bordetella avium* and Expression of the Gene in *Salmonella typhimurium*," Journal of Bacteriology, 174(23):7729-7742, Dec. 1992.
Jameson and Wolf, "The antigenic index: a novel algorithm for predicting antigenic determinants," Computer Application Bioscience, 4(1):181-186, 1988.
McGuire et al., "Nasal Immunization with Homogenate and Peptide Antigens Induces Protective Immunity against *Trichinella spiralis*," Infection and Immunity, 70(12):7149-7152, Dec. 2002.
McMichael, "Progress toward the development of a vaccine to prevent *Moraxella (Branhamella) catarrhalis* infections," Microbes and Infection, 2:561-568, 2000.
Pinchuk et al., "A CD8+ T Cell Heptaepitope Minigene Vaccine Induces Protective Immunity against *Chlamydia pneumoniae*," The Journal of Immunology, 174:5729-5739, 2005.
Wan et al., "Epitope Map for a Growth Hormone Receptor Agonist Monoclonal Antibody, MAb 263," Molecular Endocrinology, 17(11):2240-2250, 2003.

* cited by examiner

*Primary Examiner*—Shanon A. Foley
*Assistant Examiner*—Padma v Baskar
(74) *Attorney, Agent, or Firm*—Seed IP Law Group PLLC

(57) ABSTRACT

The present invention relates to polypeptides of *Moraxella (Branhamella) catarrhalis* which may be useful for prophylaxis, diagnosis and/or therapy purposes.

```
  1 ATGGACACTG ACATGAAACA TTTAACAAAA CATCGCCTAT
    CAGCTGCCAT

51 CATTGGCGTT TTATTATTCA TTAGCCCATC AGTGCAAGCA
    AATACGACAC

101 ACCATCACAC GCTAACCAGT AGCGAGCTTA AACTTGCTGA
    TGATAGTATT

151 ATTGATAGTA TCAATCAATT GGGTGAGCTG ACCGTCAATA
    TTCCAAATAC

201 ACAATATTTT CAAACCAACA ACGGTGTGAG CGTTGCTTTT
    ACGCCATTAC

251 ATGAGCTGCC TATTGTCGAT ATCAGCTTGT ATTTTAATGC
    AGGGTCAGCG

301 TATCACCATC AGGTTGGCAA ATCAGGCACG GCTAACATGG
    TTGCAACCAT
```

-continued

```
 351 GCTCACCCAA GGAACTGACA GCCTTTCTGA AGATGAGTTT
     GTTGCTGCCA
 401 AAGAGCGTCT TCGCATTCAT TTTACCAGTA CAGCAAATAA
     GGATAACTTA
 451 ACTTTATCAT TAAGAAGCTT GTCTGATCAA TCATTATTAA
     ATCAAGCCGC
 501 CGATTTAATG GTCGATGCTG TCACTCAACC TGCTTTTGAT
     GATAAGACTC
 551 TACAACGCAA CAAAAATCAG CTCATCACCA GTTTAAAACA
     AAAAAAGCAA
 601 AACCCTTATC ATGTAGCTTC TGTTGCTTAT CATCAAGCCG
     TATATGAAAA
 651 TCATCCTTAT GCACACGCAA CCACAGGCGA TGAAGATAGT
     ATTGCCAAAA
 701 TTGATCGTGA TGAGCTGCTT AATTTTTGGC ATACTTTTAT
     TAATGCAAAT
 751 AATGCGACAC TGCTGATTAC AGGTGATATG ACCGCCGAGC
     AAGCCAAATC
 801 ACTTGCCAAC CATCTGACCG CCAAATTACC CACAGGCAAG
     TCGTATAAAA
 851 ATACGCTGGA TTTGACAAAA CCAGTTAAGG CTCGTCATAT
     CCATATTCCT
```

-continued

```
 901 CACAACAGTA GTCAAACCCA AATCATCATC GGTCATCCCA
     CCAGTAAAGT
 951 ACGCACGGAC AAAGCAGGTC GTCAAGAGTT CAGCGATTTT
     TCATTAGCTA
1001 ATGAAATTTT GGCAGGTGGT GATTTTAATG CCAGATTGAT
     GAAAACCATT
1051 CGAGAGCAAA AAGGCTACAC TTATGGCATT TATGGCGGTA
     TGGAACGCCT
1101 CAGAGCAGGT GGTAATTATG TGGTTGAATT TTCAACCGAT
     GGCGATAAAG
1151 CAGCCGATGC CATTTTAGAG ACGCTACACA TCATTAATCA
     GTCGCTGAAT
1201 GAAGGCATAA CCCAAGAAGA GCTTGAGTTG GTGCGTTTGG
     GCAATAAAAA
1251 TGGTTTTGCC AATATTTTTT CAAGCAATGC CAGTATTCAT
     CGTGTCATTC
1301 GTGCTTTATT TGTTGCCGAT TATCCAAAAG ATCATCTTAA
     CCATACGCTC
1351 AATCGCTTGG ATAATGCCAC GATAAATAGT GTTAATACCG
     CACTGAACTT
1401 GCGTATCAAG CCTGATGAAT TTATCATCAT CACCGTGGGT
     AAAACTAAGC
1451 CAAATTTGGA CAAATAA
```

7 Claims, 8 Drawing Sheets

Figure 1 (SEQ ID NO: 1)

```
   1 ATGGACACTG ACATGAAACA TTTAACAAAA CATCGCCTAT CAGCTGCCAT
  51 CATTGGCGTT TTATTATTCA TTAGCCCATC AGTGCAAGCA AATACGACAC
 101 ACCATCACAC GCTAACCAGT AGCGAGCTTA AACTTGCTGA TGATAGTATT
 151 ATTGATAGTA TCAATCAATT GGGTGAGCTG ACCGTCAATA TTCCAAATAC
 201 ACAATATTTT CAAACCAACA ACGGTGTGAG CGTTGCTTTT ACGCCATTAC
 251 ATGAGCTGCC TATTGTCGAT ATCAGCTTGT ATTTTAATGC AGGGTCAGCG
 301 TATGACCATC AGGTTGGCAA ATCAGGCACG GCTAACATGG TTGCAACCAT
 351 GCTCACCCAA GGAACTGACA GCCTTTCTGA AGATGAGTTT GTTGCTGCCA
 401 AAGAGCGTCT TGGCATTGAT TTACCAGTA CAGCAAATAA GGATAACTTA
 451 ACTTTATCAT TAAGAAGCTT GTCTGATCAA TCATTATTAA ATCAAGCCGC
 501 CGATTTAATG GTCGATGCTG TCACTCAACC TGCTTTTGAT GATAAGACTC
 551 TACAACGCAA CAAAAATCAG CTCATCACCA GTTTAAAACA AAAAAAGCAA
 601 AACCCTTATC ATGTAGCTTC TGTTGCTTAT CATCAAGCCG TATATGAAAA
 651 TCATCCTTAT GCACACGCAA CCACAGGCGA TGAAGATAGT ATTGCCAAAA
 701 TTGATCGTGA TGAGCTGCTT AATTTTTGGC ATACTTTTAT TAATGCAAAT
 751 AATGCGACAC TGGTGATTAC AGGTGATATG ACCGCCGAGC AAGCCAAATC
 801 ACTTGCCAAC CATCTGACCG CCAAATTACC GACAGGCAAG TCGTATAAAA
 851 ATACGCTGGA TTTGACAAAA CCAGTTAAGG CTCGTCATAT CCATATTCCT
 901 CACAACAGTA GTCAAACCCA AATCATCATC GGTCATCCCA CCAGTAAAGT
 951 ACGCACGGAC AAAGCAGGTC GTCAAGAGTT CAGCGATTTT TCATTAGGTA
1001 ATGAAATTTT GGCAGGTGGT GATTTTAATG CCAGATTGAT GAAAACCATT
1051 CGAGAGCAAA AAGGCTACAC TTATGGCATT TATGGCGGTA TGGAACGCCT
1101 CAGAGCAGGT GGTAATTATG TGGTTGAATT TTCAACCGAT GGCGATAAAG
1151 CAGCCGATGC CATTTTAGAG ACGCTACACA TCATTAATGA GTCGCTGAAT
1201 GAAGGCATAA CCCAAGAAGA GCTTGAGTTG GTGCGTTTGG GCAATAAAAA
1251 TGGTTTTGCC AATATTTTTT CAAGCAATGC CAGTATTCAT CGTGTCATTG
1301 GTGCTTTATT TGTTGCCGAT TATCCAAAAG ATCATCTTAA CCATACGCTC
1351 AATCGCTTGG ATAATGCCAC GATAAATAGT GTTAATACCG CACTGAACTT
1401 GCGTATCAAG CCTGATGAAT TTATCATCAT CACCGTGGGT AAAACTAAGC
1451 CAAATTTGGA CAAATAA
```

Figure 2 (SEQ ID NO: 2)

```
  1 MDTDMKHLTK HRLSAAIIGV LLFISPSVQA NTTHHHTLTS SELKLADDSI
 51 IDSINQLGEL TVNIPNTQYF QTNNGVSVAF TPLHELPIVD ISLYFNAGSA
101 YDHQVGKSGT ANMVATMLTQ GTDSLSEDEF VAAKERLGID FTSTANKDNL
151 TLSLRSLSDQ SLLNQAADLM VDAVTQPAFD DKTLQRNKNQ LITSLKQKKQ
201 NPYHVASVAY HQAVYENHPY AHATTGDEDS IAKIDRDELL NFWHTFINAN
251 NATLVITGDM TAEQAKSLAN HLTAKLPTGK SYKNTLDLTK PVKARHIHIP
301 HNSSQTQIII GHPTSKVRTD KAGRQEFSDF SLGNEILAGG DFNARLMKTI
351 REQKGYTYGI YGGMERLRAG GNYVVEFSTD GDKAADAILE TLHIINESLN
401 EGITQEELEL VRLGNKNGFA NIFSSNASIH RVIGALFVAD YPKDHLNHTL
451 NRLDNATINS VNTALNLRIK PDEFIIITVG KTKPNLDK*
```

Figure 3 (SEQ ID NO: 3)

```
  1 GAGCTTAAAC TTGCTGATGA TAGTATTATT GATAGTATCA ATCAATTGGG
 51 TGAGCTGACC GTCAATATTC CAAATACACA ATATTTTCAA ACCAACAACG
101 GTGTGAGCGT TGCTTTTACG CCATTACATG AGCTGCCTAT TGTCGATATC
151 AGCTTGTATT TTAATGCAGG GTCAGCGTAT GACCATCAGG TTGGCAAATC
201 AGGCACGGCT AACATGGTTG CAACCATGCT CACCCAAGGA ACTGACAGCC
251 TTTCTGAAGA TGAGTTTGTT GCTGCCAAAG AGCGTCTTGG CATTGATTTT
301 ACCAGTACAG CAAATAAGGA TAACTTAACT TTATCATTAA GAAGCTTGTC
351 TGATCAATCA TTATTAAATC AAGCCGCCGA TTTAATGGTC GATGCTGTCA
401 CTCAACCTGC TTTTGATGAT AAGACTCTAC AACGCAACAA AAATCAGCTC
451 ATCACCAGTT TAAAACAAAA AAAGCAAAAC CCTTATCATG TAGCTTCTGT
501 TGCTTATCAT CAAGCCGTAT ATGAAAATCA TCCTTATGCA CACGCAACCA
551 CAGGCGATGA AGATAGTATT GCCAAAATTG ATCGTGATGA GCTGCTTAAT
601 TTTTGGCATA CTTTTATTAA TGCAAATAAT GCGACACTGG TGATTACAGG
651 TGATATGACC GCCGAGCAAG CCAAATCACT TGCCAACCAT CTGACCGCCA
701 AATTACCGAC AGGCAAGTCG TATAAAAATA CGCTGGATTT GACAAAACCA
751 GTTAAGGCTC GCCATATCCA TATTCCTCAC AACAGTAGTC AAACCCAAAT
801 CATCATCGGT CACCCCACCA GTAAAGTACG CACGGACAAA GCAGGTCGTC
```

Figure 3 (SEQ ID NO: 3) (continued)

```
 851 AAGAGTTCAG CGATTTTTCA TTAGGTAATG AAATTTTGGC AGGTGGTGAT
 901 TTTAATGCCA GATTGATGAA AACCATTCGA GAGCAAAAAG GCTACACTTA
 951 TGGCATTTAT GGCGGTATGG AACGCCTCAG AGCAGGTGGT AATTATGTGG
1001 TTGAATTTTC AACCGATGGC GATAAAGCAG CCGATGCCAT TTTAGAGACG
1051 CTACACATCA TTAATGAGTC GCTGAATGAA GGCATAACCC AAGAAGAGCT
1101 TGAATTGGTG CGTTTGGGTA ATAAAAATGG TTTTGCCAAT ATTTTTTCAA
1151 GCAATGCCAG TATTCATCGT GTCATTGGTG CTTTATTTGT TGCCGATTAT
1201 CCAAAAGATC ATCTTAACCA TACGCTCAAT CGCTTGGATA ATGCCACGAT
1251 AAATAGTGTT AATACCGCAC TGAACTTGCG TATCAAGCCT GATGAATTT
```

Figure 4 (SEQ ID NO: 4)

```
  1 ELKLADDSII DSINQLGELT VNIPNTQYFQ TNNGVSVAFT PLHELPIVDI
 51 SLYFNAGSAY DHQVGKSGTA NMVATMLTQG TDSLSEDEFV AAKERLGIDF
101 TSTANKDNLT LSLRSLSDQS LLNQAADLMV DAVTQPAFDD KTLQRNKNQL
151 ITSLKQKKQN PYHVASVAYH QAVYENHPYA HATTGDEDSI AKIDRDELLN
201 FWHTFINANN ATLVITGDMT AEQAKSLANH LTAKLPTGKS YKNTLDLTKP
251 VKARHIHIPH NSSQTQIIIG HPTSKVRTDK AGRQEFSDFS LGNEILAGGD
301 FNARLMKTIR EQKGYTYGIY GGMERLRAGG NYVVEFSTDG DKAADAILET
351 LHIINESLNE GITQEELELV RLGNKNGFAN IFSSNASIHR VIGALFVADY
401 PKDHLNHTLN RLDNATINSV NTALNLRIKP DEF
```

Figure 5 (SEQ ID NO: 5)

```
   1 GAGCTTAAAC TTGCTGATGA TAGTATTATT GATAGTATCA ATCAATTGGG
  51 TGAGCTGACC GTCAATATTC CAAATACACA ATATTTTCAA ACCAACAACG
 101 GTGTGAGCGT TGCTTTTACG CCATTACATG AGCTGCCTAT TGTCGATATC
 151 AGCTTGTATT TTAATGCAGG GTCAGCGTAT GACCATCAGG TTGGCAAATC
 201 AGGCACGGCT AACATGGTTG CAACCATGCT CACCCAAGGA ACTGACAGCC
 251 TTTCTGAAGA TGAGTTTGTT GCTGCCAAAG AGCGTCTTGG CATTGATTTT
 301 ACCAGTACAG CAAATAAGGA TAACTTAACT TTATCATTAA GAAGCTTGTC
 351 TGATCAATCA TTATTAAATC AAGCCGCCGA TTTAATGGTC GATGCTGTCA
 401 CTCAACCTGC TTTTGATGAT AAGACTCTAC AACGCAACAA AAATCAGCTC
 451 ATCACCAGTT TAAAACAAAA AAAGCAAAAC CCTTATCATG TAGCTTCTGT
 501 TGCTTATCAT CAAGCCGTAT ATGAAAATCA TCCTTATGCA CACGCAACCA
 551 CAGGCGATGA AGATAGTATT GCCAAAATTG ATCGTGATGA GCTGCTTAAT
 601 TTTTGGCATA CTTTTATTAA TGCAAATAAT GCGACACTGG TGATTACAGG
 651 TGATATGACC GCCGAGCAAG CCAAATCACT TGCCAACCAT CTGACCGCCA
 701 AATTACCGAC AGGCAAGTCT TATAAAAATA CGCTGGATTT GACAAAACCA
 751 GTTAAGGCTC GCCATATCCA TATTCCTCAC AACAGTAGTC AAACCCAAAT
 801 CATCATCGGT CACCCCACCA GTAAAGTACG CACGGACAAA GCAGGTCGTC
 851 AAGAGTTCAG CGATTTTTCA TTAGGTAATG AAATTTTGGC AGGTGGTGAT
 901 TTTAATGCCA GATTGATGAA AACCATTCGA GAGCAAAAAG GCTACACTTA
 951 TGGCATTTAT GGCGGTATGG AACGCCTCAG AGCAGGTGGT AATTATGTGG
1001 TTGAATTTTC AACCGATGGC GATAAAGCAG CCGATGCCAT TTTAGAGACG
1051 CTACACATCA TTAATGAGTC GCTGAATGAA GGCATAACCC AAGAAGAGCT
1101 TGAGTTGGTG CGTTTGGGCA ATAAAAATGG TTTTGCCAAT ATTTTTTCAA
1151 GCAATGCCAG TATTCATCGT GTCATTGGTG CTTTATTTGT TGCCGATTAT
1201 CCAAAAGATC ATCTTAACCA TACGCTCAAT CGCTTGGATA ATGCCACGAT
1251 AAATAGTGTT AATACCGCAC TGAACTTGCG TATCAAGCCT GATGAATTT
```

Figure 6 (SEQ ID NO: 6)

```
  1 ELKLADDSII DSINQLGELT VNIPNTQYFQ TNNGVSVAFT PLHELPIVDI
 51 SLYFNAGSAY DHQVGKSGTA NMVATMLTQG TDSLSEDEFV AAKERLGIDF
101 TSTANKDNLT LSLRSLSDQS LLNQAADLMV DAVTQPAFDD KTLQRNKNQL
151 ITSLKQKKQN PYHVASVAYH QAVYENHPYA HATTGDEDSI AKIDRDELLN
201 FWHTFINANN ATLVITGDMT AEQAKSLANH LTAKLPTGKS YKNTLDLTKP
251 VKARHIHIPH NSSQTQIIIG HPTSKVRTDK AGRQEFSDFS LGNEILAGGD
301 FNARLMKTIR EQKGYTYGIY GGMERLRAGG NYVVEFSTDG DKAADAILET
351 LHIINESLNE GITQEELELV RLGNKNGFAN IFSSNASIHR VIGALFVADY
```

Figure 6 (SEQ ID NO: 6) (continued)

```
401 PKDHLNHTLN RLDNATINSV NTALNLRIKP DEF
```

Figure 7 (SEQ ID NO: 7)

```
   1 GAGCTTAAAC TTGCTGATGA TAGTATTATT GATAGTATCA ATCAATTGGG
  51 TGAGCTGACC GTCAATATTC CAAATACACA ATATTTCAA ACCAACAACG
 101 GTGTGAGCGT TGCTTTTACG CCATTACATG AGCTGCCTAT TGTCGATATC
 151 AGCTTGTATT TTAATGCAGG GTCAGCGTAT GACCATCAGG TTGGCAAATC
 201 AGGCACGGCT AACATGGTTG CAACCATGCT CACCCAAGGA ACTGACAGCC
 251 TTTCTGAAGA TGAGTTTGTT GCTGCCAAAG AGCGTCTTGG CATTGATTTT
 301 ACCAGTACAG CAAATAAGGA TAACTTAACT TTATCATTAA GAAGCTTGTC
 351 TGATCAATCA TTATTAAATC AAGCCGCCGA TTTAATGGTC GATGCTGTCA
 401 CTCAACCTGC TTTTGATGAT AAGACTCTAC AACGCAACAA AAATCAGCTC
 451 ATCACCAGTT TAAAACAAAA AAAGCAAAAC CCTTATCATG TAGCTTCTGT
 501 TGCTTATCAT CAAGCCTAT ATGAAAATCA TCCTTATGCA CACGCAACCA
 551 CAGGCGATGA AGATAGTATT GCCAAAATTG ATCGTGATGA GCTGCTTAAT
 601 TTTTGGCATA CTTTTATTAA TGCAAATAAT GCGACACTGG TGATTACAGG
 651 TGATATGACC GCCGAGCAAG CCAAATCACT TGCCAACCAT CTGACCGCCA
 701 AATTACCGAC AGGCAAGTCG TATAAAAATA CGCTGGATTT GACAAAACCA
 751 GTTAAGGCTC GCCATATCCA TATTCCTCAC AACAGTAGTC AAACCCAAAT
 801 CATCATCGGT CACCCCACCA GTAAAGTACG CACGGACAAA GCAGGTCGTC
 851 AAGAGTTCAG CGATTTTTCA TTAGGTAATG AAATTTTGGC AGGTGGTGAT
 901 TTTAATGCCA GATTGATGAA AACCATTCGA GAGCAAAAAG GCTACACTTA
 951 TGGCATTTAT GGCGGTATGG AACGCCTCAG AGCAGGTGGT AATTATGTGG
1001 TTGAATTTTC AACCGATGGC GATAAAGCAG CCGATGCCAT TTTAGAGACG
1051 CTACACATCA TTAATGAGTC GCTGAATGAA GGCATAACCC AAGAAGAGCT
1101 TGAATTGGTG CGTTTGGGTA ATAAAAATGG TTTTGCCAAT ATTTTTTCAA
1151 GCAATGCCAG TATTCATCGT GTCATTGGTG CTTTATTTGT TGCCGATTAT
1201 CCAAAAGACC ATCTTAACCA TACGCTCAAT CGCTTGGATA ATGCCACGAT
1251 AAATAGTGTT AATACCGCAC TGAACTTGCG TATCAAGCCT GATGAATTT
```

Figure 8 (SEQ ID NO: 8)

```
   1 ELKLADDSII DSINQLGELT VNIPNTQYFQ TNNGVSVAFT PLHELPIVDI
  51 SLYFNAGSAY DHQVGKSGTA NMVATMLTQG TDSLSEDEFV AAKERLGIDF
 101 TSTANKDNLT LSLRSLSDQS LLNQAADLMV DAVTQPAFDD KTLQRNKNQL
 151 ITSLKQKKQN PYHVASVAYH QAVYENHPYA HATTGDEDSI AKIDRDELLN
 201 FWHTFINANN ATLVITGDMT AEQAKSLANH LTAKLPTGKS YKNTLDLTKP
 251 VKARHIHIPH NSSQTQIIIG HPTSKVRTDK AGRQEFSDFS LGNEILAGGD
 301 FNARLMKTIR EQKGYTYGIY GGMERLRAGG NYVVEFSTDG DKAADAILET
 351 LHIINESLNE GITQEELELV RLGNKNGFAN IFSSNASIHR VIGALFVADY
 401 PKDHLNHTLN RLDNATINSV NTALNLRIKP DEF
```

Figure 9 (SEQ ID NO: 9)

```
   1 ATGAGCTTAA TTAATAAATT AAATGAACGC ATTACGCCGC ATGTCTTAAC
  51 TTCGATTAAA AATCAAGATG GCGATAATGC TGATAAATCT AATTTGTTAA
 101 CCGCATTTTA TACCATTTTT GCAGGACGTC TGAGTAATGA AGATGTGTAT
 151 CAGCGTGCCA ATGCTTTGCC TGATAATGAG CTTGAGCATG GCATCATCT
 201 GCTCAATGTT GCTTTTAGTG ATGTTCAAC TGGTGAAGAT CAGATTGCTT
 251 CTTTGAGTAA TCAATTAGCC GATGAATATC ATGTTTCGCC AGTAACGGCA
 301 CGCACCGCAA TCGCAACGGC AGCACCTTTG CTTTGGCAC GCATTAAAGA
 351 GCAAGCAGGT GCATTATCTG TACCGTCTTT TATTCGTACT CAATTGGCTA
 401 AAGAAGAAAA CCGTTTGCCA ACTTGGGCGC ATACTTTATT GCCAGCAGGG
 451 CTATTTGCAA CCGCTGCCAC AACCACCGCC GAGCCTGTAA CGACAGCCTC
 501 TGCTGTTGTG AAAGAGCCTG TCAAACCAAG TGTTGTGACA GAACCAGTTC
 551 ATCCAGCTGC GGCTACCACC CCAGTCAAAA CACCAACTGC CCAGCATTAC
 601 GAAAACAAAG AAAAAGTCC TTTCTAAAA ACGATTCTAC CGATTATTGG
 651 ATTGATTATT TTGCAGGCT TGGCATGGCT TTGTTAAGA GCATGTCAAG
 701 ACAAACCAAC ACCTGTTGCG GCACCTGTTG CGACAGATAC AGCACCTGTG
 751 GTAGCGGATA ATGCTGTACA GGCAGACCCA ACACAAACAG GTGTTGCCCA
 801 AGCACCTGCA ACGCTTAGCT TGTCTGTTGA TGAAACGGGT CAAGCGTTGT
 851 ACTCGCACCG TGCTCAGGTT GGTAGTGAAG AGCTTGCAGG TCATATCCGT
```

Figure 9 (SEQ ID NO: 9) (continued)

```
 901 GCAGCTATTG CTCAAGTCTT TGGCGTACAA GATTTAACCA TTCAAAATAC
 951 CAATGTACAT ACCGCTACGA TGCCAGCGGC AGAATACTTA CCAGCAATTT
1001 TGGGTTTGAT GAAAGGTGTA CCAAATTCAA GCGTTGTGAT TCATGATCAT
1051 ACGGTACGCT TTAATGCAAC CACGCCAGAA GATGTAGCAA AACTGGTAGA
1101 GGGTGCTAAA AATATTCTAC CCGCTGATTT TACTGTAGAA GCAGAACCTG
1151 AACTTGATAT TAATACTGCG GTTGCCGATA GTATTGAAAC AGCGCGTGTT
1201 GCTATTGTTG CTTTGGGTGA TACGGTTGAA GAAAATGAGA TGGATATTTT
1251 AATCAATGCA TTAAATACCC AAATCATTAA CTTTGCTTTA GACTCAACCG
1301 AAATTCCCCA AGAAAATAAA GAAATCTTGG ATTTGGCTGC CGAAAAATTA
1351 AAGGCAGTGC CTGAAACAAC TTTGCGTATC ATTGGTCATA CAGACACTCA
1401 AGGCACACAT GAGTATAATC AAGATTTATC AGAATCTCGT GCTGCTGCTG
1451 TTAAAGAGTA TTTGGTATCA AAAGGTGTTG CTGCTAACG CTTGAACACT
1501 CAAGGTGCAA GTTTTGATTA TCCAGTTGCA TCAAATGCTA CCGAACAAGG
1551 TCGCTTCCAA AACCGTCGTA TTGAGTTTGT ACTTTTCCAA GAAGGTGAAG
1601 CAATTACTCA AGTCGGTCAT GCTGAAGATG CACCAACACC TGTTGCACAA
1651 AACTGA
```

Figure 10 (SEQ ID NO: 10)

```
  1 MSLINKLNER ITPHVLTSIK NODGDNADKS NLLTAFYTIF AGRLSNEDVY
 51 QRANALPDNE LEHGHHLLNV AFSDVSTGED QIASLSNQLA DEYHVSPVTA
101 RTAIATAAPL ALARIKEQAG ALSVPSFIRT QLAKEENRLP TWAHTLLPAG
151 LFATAATTTA EPVTTASAVV KEPVKPSVVT EPVHPAAATT PVKTPTAQHY
201 ENKEKSPFLK TILPIIGLII FAGLAWLLLR ACQDKPTPVA APVATDTAPV
251 VADNAVQADP TQTGVAQAPA TLSLSVDETG QALYSHRAQV GSEELAGHIR
301 AAIAQVFGVQ DLTIQNTNVH TATMPAAEYL PAILGLMKGV PNSSVVIHDH
351 TVRFNATTPE DVAKLVEGAK NILPADFTVE AEPELDINTA VADSIETARV
401 AIVALGDTVE ENEMDILINA LNTQIINFAL DSTEIPQENK EILDLAAEKL
451 KAVPETTLRI IGHTDTQGTH EYNQDLSESR AAAVKEYLVS KGVAAERLNT
501 QGASFDYPVA SNATEQGRFQ NRRIEFVLFQ EGEAITQVGH AEDAPTPVAQ
551 N*
```

Figure 11 (SEQ ID NO: 11)

```
   1 ATGGATACAA AACACATTCA GCAAAATTGG CTTCTACCTG ATGGTGTGGC
  51 TGATGTACTA TTTACCGATG CTCAAAAACA AGAAAGCCTG CGTGATGCCT
 101 TGCTATTTGT GCTAACCGCA CACGGTTATC GCTTGGTGTC ACCACCATTA
 151 ATAGAGTATA CCGAAAGTCT GCTAAATAAT GCTGACGAAG ATCTAAAACG
 201 CCAAACTTTC AAATTTATCG ATCAGCTCAA TGGTCGTTTG ATGGGTTTGC
 251 GTGCCGATAT TACGCCACAA ATTCTACGCA TTGATAGCAA ATATGGTCAA
 301 GGCATCAGCC GTTACTGTTA TGTTGGGCAA GTTGTCAAAA CCCTACCGAC
 351 TGGTCTGTTT GGGCTGCGTA CACCGCTTCA ATTGGGTGCT GAGATTTTTG
 401 GGATAGATGA TATCCGTGCC GAGCTTGAGC TGATTGATCT ATTGGCCGCA
 451 TTGGCAGATG AGATCGGACT AGGCCGAGAG ATGCTACATG TGGATATTGG
 501 TCATGTCGCT ATTTTTGATC GCTTGTGTCA GTTGCATGGC GTTTCAAATA
 551 AAGATGCTGA TGAGCTGATT GGCATTTACC ATAAAAAAGC CATGCCAGAA
 601 CTTGCCAAAT GGTGCCAAAA TATTGGCAAT AGCCTAAACA GCCCAAGCGA
 651 TGCAACCGAT TTTTTGGTAT TGGCTAAGCA TACATTAAGC AGTGATCGGA
 701 CACCAAATGC CGAGGCTTTA TTAAGTAAAC TGTCCGATAA AGCTCGCCAA
 751 GATAATAAAA TCATCCAAGC GGCAAATGAG CTTGCTACTT TGGCGGCACA
 801 TATCAGAGCG GTGGGATGA GTGTGAGTAT TGATGTGACT GAATTGTCAG
 851 GATATCATTA TCATACTGGT GTGGTATTTA ATGTCTATTT GGGTAATAGA
 901 ACCACACAGA CTCAAGCTTT GGTACGAGGC GGTCGCTTTG ATGGTATCTC
 951 AACTCACAGC GTAGCAAGGG GCGCAACTGG TTTTAGCATG GATATTAATC
1001 GTTTGCTTGA ATTTGTAGAG CTTGAAGAAG ATACTGTGAT TTTGGTGGAT
1051 TATCACGATT TGCAAAATGC TGATGCAGAC ACAAAAGCTG ATTTGGCCAC
1101 ACAAATTAAA ACCTTGCAAT CTGAAGGCTG TATTGTCATT AAGCCTTTGA
1151 CTGTAGATGA TAAGCCTAAC CAGATTGATG GTGTTTTGCA TTGGGACACC
1201 GATCAAGATA AGCCGATTTG GCGGTGCGA TTAGTTGGTG ATGAGTACTA
1251 A
```

Figure 12 (SEQ ID NO: 12)

```
  1 MDTKHIQQNW LLPDGVADVL FTDAQKQESL RDALLFVLTA HGYRLVSPPL
 51 IEYTESLLNN ADEDLKRQTF KFIDQLNGRL MGLRADITPQ ILRIDSKYGQ
101 GISRYCYVGQ VVKTLPTGLF GLRTPLQLGA EIFGIDDIRA ELELIDLLAA
151 LADEIGLGRE MLHVDIGHVA IFDRLCQLHG VSNKDADELI GIYHKKAMPE
201 LAKWCQNIGN SLNSPSDATD FLVLAKHTLS SDRTPNAEAL LSKLSDKARQ
251 DNKIIQAANE LATLAAHIRA VGMSVSIDVT ELSGYHYHTG VVFNVYLGNR
301 TTQTQALVRG GRFDGISTHS VARGATGFSM DINRLLEFVE LEEDTVILVD
351 YHDLQNADAD TKADLATQIK TLQSEGCIVI KPLTVDDKPN QIDGVLHWDT
401 DQDKPIWAVR LVGDEY*
```

Figure 13 (SEQ ID NO: 13)

```
  1 ATGAATAATT TTGTGTATCA GCTACAAAGT TTTTGGTATG AGCTTAATCA
 51 GGTCAATCGT CATACCATTG CTCAATCACC CAAATATATA CAGCTGACGG
101 TACTTGGTTT GATCGTGATG ATCATTGGCA TTTTTGGCTG GCTACTTGCG
151 ATTTTACCAA CCATTCAAAA GCTTAATGCA GCCCAAAGTC AAGAATCTGC
201 CTTAATTGAT GAATTTGCCA CTAAATATCA TAAAGCCCAG CAGTTTGACC
251 ATCTAAGCCA TCAGGTCATA CAAAAAAATA CACAACTTGA AAATCAGCTC
301 AATGCTCTGC CACGCACAGC ACCGATGAGC GAGATTATCG GAATGATAAA
351 TACCAAAGCA CAAGCGGTTA ATGTGCAGGT GGTGAGTGCA TCAGTTCAAG
401 CAGGTCGTGA ACAGGATTAT TATACCGAAC GCCCTATCGC AGTGAGTGCG
451 ACAGGGGATT ATCATGCTTT GGGTCGATGG TTACTTGAGT TGTCAGAGGC
501 TAACCATTTG CTGACAGTGC ATGATTTTGA TCTGAAGGCT GGTTTGAACC
551 ATCAGCTGAT GATGATTGCT CAGATGAAAA CTTATCAAGC AAACAAACGC
601 CCAAAACCAG TTGCTCAGCA GGTGCCTGAT GTTCAATGA
```

Figure 14 (SEQ ID NO: 14)

```
  1 MNNFVYQLQS FWYELNQVNR HTIAQSPKYI QLTVLGLIVM IIGIFGWLLA
 51 ILPTIQKLNA AQSQESALID EFATKYHKAQ QFDHLSHQVI QKNTQLENQL
101 NALPRTAPMS EIIGMINTKA QAVNVQVVSA SVQAGREQDY YTERPIAVSA
151 TGDYHALGRW LLELSEANHL LTVHDFDLKA GLNHQLMMIA QMKTYQANKR
201 PKPVAQQVPD VQ*
```

Figure 15

```
ETSU C-2    1 GAGCTTAAACTTGCTGATGATAGTATTATTGATAGTATCAATCAATTGGG  50
ETSU 658    1 GAGCTTAAACTTGCTGATGATAGTATTATTGATAGTATCAATCAATTGGG  50
ETSU T-25   1 GAGCTTAAACTTGCTGATGATAGTATTATTGATAGTATCAATCAATTGGG  50
M-12        1 GAGCTTAAACTTGCTGATGATAGTATTATTGATAGTATCAATCAATTGGG  50
              **************************************************

ETSU C-2   51 TGAGCTGACCGTCAATATTCCAAATACACAATATTTTCAAACCAACAACG 100
ETSU 658   51 TGAGCTGACCGTCAATATTCCAAATACACAATATTTTCAAACCAACAACG 100
ETSU T-25  51 TGAGCTGACCGTCAATATTCCAAATACACAATATTTTCAAACCAACAACG 100
M-12       51 TGAGCTGACCGTCAATATTCCAAATACACAATATTTTCAAACCAACAACG 100
              **************************************************

ETSU C-2  101 GTGTGAGCGTTGCTTTTACGCCATTACATGAGCTGCCTATTGTCGATATC 150
ETSU 658  101 GTGTGAGCGTTGCTTTTACGCCATTACATGAGCTGCCTATTGTCGATATC 150
ETSU T-25 101 GTGTGAGCGTTGCTTTTACGCCATTACATGAGCTGCCTATTGTCGATATC 150
M-12      101 GTGTGAGCGTTGCTTTTACGCCATTACATGAGCTGCCTATTGTCGATATC 150
              **************************************************

ETSU C-2  151 AGCTTGTATTTTAATGCAGGGTCAGCGTATGACCATCAGGTTGGCAAATC 200
ETSU 658  151 AGCTTGTATTTTAATGCAGGGTCAGCGTATGACCATCAGGTTGGCAAATC 200
ETSU T-25 151 AGCTTGTATTTTAATGCAGGGTCAGCGTATGACCATCAGGTTGGCAAATC 200
M-12      151 AGCTTGTATTTTAATGCAGGGTCAGCGTATGACCATCAGGTTGGCAAATC 200
              **************************************************
```

Figure 15 (continued)

```
ETSU C-2    201 AGGCACGGCTAACATGGTTGCAACCATGCTCACCCAAGGAACTGACAGCC 250
ETSU 658    201 AGGCACGGCTAACATGGTTGCAACCATGCTCACCCAAGGAACTGACAGCC 250
ETSU T-25   201 AGGCACGGCTAACATGGTTGCAACCATGCTCACCCAAGGAACTGACAGCC 250
M-12        201 AGGCACGGCTAACATGGTTGCAACCATGCTCACCCAAGGAACTGACAGCC 250
                **************************************************

ETSU C-2    251 TTTCTGAAGATGAGTTTGTTGCTGCCAAAGAGCGTCTTGGCATTGATTTT 300
ETSU 658    251 TTTCTGAAGATGAGTTTGTTGCTGCCAAAGAGCGTCTTGGCATTGATTTT 300
ETSU T-25   251 TTTCTGAAGATGAGTTTGTTGCTGCCAAAGAGCGTCTTGGCATTGATTTT 300
M-12        251 TTTCTGAAGATGAGTTTGTTGCTGCCAAAGAGCGTCTTGGCATTGATTTT 300
                **************************************************

ETSU C-2    301 ACCAGTACAGCAAATAAGGATAACTTAACTTTATCATTAAGAAGCTTGTC 350
ETSU 658    301 ACCAGTACAGCAAATAAGGATAACTTAACTTTATCATTAAGAAGCTTGTC 350
ETSU T-25   301 ACCAGTACAGCAAATAAGGATAACTTAACTTTATCATTAAGAAGCTTGTC 350
M-12        301 ACCAGTACAGCAAATAAGGATAACTTAACTTTATCATTAAGAAGCTTGTC 350
                **************************************************

ETSU C-2    351 TGATCAATCATTATTAAATCAAGCCGCCGATTTAATGGTCGATGCTGTCA 400
ETSU 658    351 TGATCAATCATTATTAAATCAAGCCGCCGATTTAATGGTCGATGCTGTCA 400
ETSU T-25   351 TGATCAATCATTATTAAATCAAGCCGCCGATTTAATGGTCGATGCTGTCA 400
M-12        351 TGATCAATCATTATTAAATCAAGCCGCCGATTTAATGGTCGATGCTGTCA 400
                **************************************************

ETSU C-2    401 CTCAACCTGCTTTTGATGATAAGACTCTACAACGCAACAAAAATCAGCTC 450
ETSU 658    401 CTCAACCTGCTTTTGATGATAAGACTCTACAACGCAACAAAAATCAGCTC 450
ETSU T-25   401 CTCAACCTGCTTTTGATGATAAGACTCTACAACGCAACAAAAATCAGCTC 450
M-12        401 CTCAACCTGCTTTTGATGATAAGACTCTACAACGCAACAAAAATCAGCTC 450
                **************************************************

ETSU C-2    451 ATCACCAGTTTAAAACAAAAAAAGCAAAACCCTTATCATGTAGCTTCTGT 500
ETSU 658    451 ATCACCAGTTTAAAACAAAAAAAGCAAAACCCTTATCATGTAGCTTCTGT 500
ETSU T-25   451 ATCACCAGTTTAAAACAAAAAAAGCAAAACCCTTATCATGTAGCTTCTGT 500
M-12        451 ATCACCAGTTTAAAACAAAAAAAGCAAAACCCTTATCATGTAGCTTCTGT 500
                **************************************************

ETSU C-2    501 TGCTTATCATCAAGCCGTATATGAAAATCATCCTTATGCACACGCAACCA 550
ETSU 658    501 TGCTTATCATCAAGCCGTATATGAAAATCATCCTTATGCACACGCAACCA 550
ETSU T-25   501 TGCTTATCATCAAGCCGTATATGAAAATCATCCTTATGCACACGCAACCA 550
M-12        501 TGCTTATCATCAAGCCGTATATGAAAATCATCCTTATGCACACGCAACCA 550
                **************************************************

ETSU C-2    551 CAGGCGATGAAGATAGTATTGCCAAAATTGATCGTGATGAGCTGCTTAAT 600
ETSU 658    551 CAGGCGATGAAGATAGTATTGCCAAAATTGATCGTGATGAGCTGCTTAAT 600
ETSU T-25   551 CAGGCGATGAAGATAGTATTGCCAAAATTGATCGTGATGAGCTGCTTAAT 600
M-12        551 CAGGCGATGAAGATAGTATTGCCAAAATTGATCGTGATGAGCTGCTTAAT 600
                **************************************************

ETSU C-2    601 TTTTGGCATACTTTTATTAATGCAAATAATGCGACACTGGTGATTACAGG 650
ETSU 658    601 TTTTGGCATACTTTTATTAATGCAAATAATGCGACACTGGTGATTACAGG 650
ETSU T-25   601 TTTTGGCATACTTTTATTAATGCAAATAATGCGACACTGGTGATTACAGG 650
M-12        601 TTTTGGCATACTTTTATTAATGCAAATAATGCGACACTGGTGATTACAGG 650
                **************************************************

ETSU C-2    651 TGATATGACCGCCGAGCAAGCCAAATCACTTGCCAACCATCTGACCGCCA 700
ETSU 658    651 TGATATGACCGCCGAGCAAGCCAAATCACTTGCCAACCATCTGACCGCCA 700
ETSU T-25   651 TGATATGACCGCCGAGCAAGCCAAATCACTTGCCAACCATCTGACCGCCA 700
M-12        651 TGATATGACCGCCGAGCAAGCCAAATCACTTGCCAACCATCTGACCGCCA 700
                **************************************************

ETSU C-2    701 AATTACCGACAGGCAAGTCGTATAAAAATACGCTGGATTTGACAAAACCA 750
ETSU 658    701 AATTACCGACAGGCAAGTCGTATAAAAATACGCTGGATTTGACAAAACCA 750
ETSU T-25   701 AATTACCGACAGGCAAGTCTTATAAAAATACGCTGGATTTGACAAAACCA 750
M-12        701 AATTACCGACAGGCAAGTCGTATAAAAATACGCTGGATTTGACAAAACCA 750
                ******************* ******************************
```

Figure 15 (continued)

```
ETSU C-2    751  GTTAAGGCTCGTCATATCCATATTCCTCACAACAGTAGTCAAACCCAAAT  800
ETSU 658    751  GTTAAGGCTCGCCATATCCATATTCCTCACAACAGTAGTCAAACCCAAAT  800
ETSU T-25   751  GTTAAGGCTCGCCATATCCATATTCCTCACAACAGTAGTCAAACCCAAAT  800
M-12        751  GTTAAGGCTCGCCATATCCATATTCCTCACAACAGTAGTCAAACCCAAAT  800
                 ********** ***************************************

ETSU C-2    801  CATCATCGGTCATCCCACCAGTAAAGTACGCACGGACAAAGCAGGTCGTC  850
ETSU 658    801  CATCATCGGTCACCCCACCAGTAAAGTACGCACGGACAAAGCAGGTCGTC  850
ETSU T-25   801  CATCATCGGTCACCCCACCAGTAAAGTACGCACGGACAAAGCAGGTCGTC  850
M-12        801  CATCATCGGTCACCCCACCAGTAAAGTACGCACGGACAAAGCAGGTCGTC  850
                 ************ *************************************

ETSU C-2    851  AAGAGTTCAGCGATTTTTCATTAGGTAATGAAATTTTGGCAGGTGGTGAT  900
ETSU 658    851  AAGAGTTCAGCGATTTTTCATTAGGTAATGAAATTTTGGCAGGTGGTGAT  900
ETSU T-25   851  AAGAGTTCAGCGATTTTTCATTAGGTAATGAAATTTTGGCAGGTGGTGAT  900
M-12        851  AAGAGTTCAGCGATTTTTCATTAGGTAATGAAATTTTGGCAGGTGGTGAT  900
                 **************************************************

ETSU C-2    901  TTTAATGCCAGATTGATGAAAACCATTCGAGAGCAAAAGGCTACACTTA   950
ETSU 658    901  TTTAATGCCAGATTGATGAAAACCATTCGAGAGCAAAAGGCTACACTTA   950
ETSU T-25   901  TTTAATGCCAGATTGATGAAAACCATTCGAGAGCAAAAGGCTACACTTA   950
M-12        901  TTTAATGCCAGATTGATGAAAACCATTCGAGAGCAAAAGGCTACACTTA   950
                 **************************************************

ETSU C-2    951  TGGCATTTATGGCGGTATGGAACGCCTCAGAGCAGGTGGTAATTATGTGG 1000
ETSU 658    951  TGGCATTTATGGCGGTATGGAACGCCTCAGAGCAGGTGGTAATTATGTGG 1000
ETSU T-25   951  TGGCATTTATGGCGGTATGGAACGCCTCAGAGCAGGTGGTAATTATGTGG 1000
M-12        951  TGGCATTTATGGCGGTATGGAACGCCTCAGAGCAGGTGGTAATTATGTGG 1000
                 **************************************************

ETSU C-2   1001  TTGAATTTTCAACCGATGGCGATAAAGCAGCCGATGCCATTTTAGAGACG 1050
ETSU 658   1001  TTGAATTTTCAACCGATGGCGATAAAGCAGCCGATGCCATTTTAGAGACG 1050
ETSU T-25  1001  TTGAATTTTCAACCGATGGCGATAAAGCAGCCGATGCCATTTTAGAGACG 1050
M-12       1001  TTGAATTTTCAACCGATGGCGATAAAGCAGCCGATGCCATTTTAGAGACG 1050
                 **************************************************

ETSU C-2   1051  CTACACATCATTAATGAGTCGCTGAATGAAGGCATAACCCAAGAAGAGCT 1100
ETSU 658   1051  CTACACATCATTAATGAGTCGCTGAATGAAGGCATAACCCAAGAAGAGCT 1100
ETSU T-25  1051  CTACACATCATTAATGAGTCGCTGAATGAAGGCATAACCCAAGAAGAGCT 1100
M-12       1051  CTACACATCATTAATGAGTCGCTGAATGAAGGCATAACCCAAGAAGAGCT 1100
                 **************************************************

ETSU C-2   1101  TGAGTTGGTGCGTTTGGGCAATAAAAATGGTTTTGCCAATATTTTTTCAA 1150
ETSU 658   1101  TGAATTGGTGCGTTTGGGTAATAAAAATGGTTTTGCCAATATTTTTTCAA 1150
ETSU T-25  1101  TGAGTTGGTGCGTTTGGGCAATAAAAATGGTTTTGCCAATATTTTTTCAA 1150
M-12       1101  TGAATTGGTGCGTTTGGGTAATAAAAATGGTTTTGCCAATATTTTTTCAA 1150
                 *** ************** *******************************

ETSU C-2   1151  GCAATGCCAGTATTCATCGTGTCATTGGTGCTTTATTTGTTGCCGATTAT 1200
ETSU 658   1151  GCAATGCCAGTATTCATCGTGTCATTGGTGCTTTATTTGTTGCCGATTAT 1200
ETSU T-25  1151  GCAATGCCAGTATTCATCGTGTCATTGGTGCTTTATTTGTTGCCGATTAT 1200
M-12       1151  GCAATGCCAGTATTCATCGTGTCATTGGTGCTTTATTTGTTGCCGATTAT 1200
                 **************************************************

ETSU C-2   1201  CCAAAAGATCATCTTAACCATACGCTCAATCGCTTGGATAATGCCACGAT 1250
ETSU 658   1201  CCAAAAGATCATCTTAACCATACGCTCAATCGCTTGGATAATGCCACGAT 1250
ETSU T-25  1201  CCAAAAGATCATCTTAACCATACGCTCAATCGCTTGGATAATGCCACGAT 1250
M-12       1201  CCAAAAGACCATCTTAACCATACGCTCAATCGCTTGGATAATGCCACGAT 1250
                 ******** *****************************************

ETSU C-2   1251  AAATAGTGTTAATACCGCACTGAACTTGCGTATCAAGCCTGATGAATTT  1299
ETSU 658   1251  AAATAGTGTTAATACCGCACTGAACTTGCGTATCAAGCCTGATGAATTT  1299
ETSU T-25  1251  AAATAGTGTTAATACCGCACTGAACTTGCGTATCAAGCCTGATGAATTT  1299
M-12       1251  AAATAGTGTTAATACCGCACTGAACTTGCGTATCAAGCCTGATGAATTT  1299
                 **************************************************
```

Figure 16

```
ETSU C-2    1   ELKLADDSIIDSINQLGELTVNIPNTQYFQTNNGVSVAFTPLHELPIVDI  50
ETSU 658    1   ELKLADDSIIDSINQLGELTVNIPNTQYFQTNNGVSVAFTPLHELPIVDI  50
ETSU T-25   1   ELKLADDSIIDSINQLGELTVNIPNTQYFQTNNGVSVAFTPLHELPIVDI  50
M-12        1   ELKLADDSIIDSINQLGELTVNIPNTQYFQTNNGVSVAFTPLHELPIVDI  50
                **************************************************

ETSU C-2    51  SLYFNAGSAYDHQVGKSGTANMVATMLTQGTDSLSEDEFVAAKERLGIDF 100
ETSU 658    51  SLYFNAGSAYDHQVGKSGTANMVATMLTQGTDSLSEDEFVAAKERLGIDF 100
ETSU T-25   51  SLYFNAGSAYDHQVGKSGTANMVATMLTQGTDSLSEDEFVAAKERLGIDF 100
M-12        51  SLYFNAGSAYDHQVGKSGTANMVATMLTQGTDSLSEDEFVAAKERLGIDF 100
                **************************************************

ETSU C-2   101  TSTANKDNLTLSLRSLSDQSLLNQAADLMVDAVTQPAFDDKTLQRNKNQL 150
ETSU 658   101  TSTANKDNLTLSLRSLSDQSLLNQAADLMVDAVTQPAFDDKTLQRNKNQL 150
ETSU T-25  101  TSTANKDNLTLSLRSLSDQSLLNQAADLMVDAVTQPAFDDKTLQRNKNQL 150
M-12       101  TSTANKDNLTLSLRSLSDQSLLNQAADLMVDAVTQPAFDDKTLQRNKNQL 150
                **************************************************

ETSU C-2   151  ITSLKQKKQNPYHVASVAYHQAVYENHPYAHATTGDEDSIAKIDRDELLN 200
ETSU 658   151  ITSLKQKKQNPYHVASVAYHQAVYENHPYAHATTGDEDSIAKIDRDELLN 200
ETSU T-25  151  ITSLKQKKQNPYHVASVAYHQAVYENHPYAHATTGDEDSIAKIDRDELLN 200
M-12       151  ITSLKQKKQNPYHVASVAYHQAVYENHPYAHATTGDEDSIAKIDRDELLN 200
                **************************************************

ETSU C-2   201  FWHTFINANNATLVITGDMTAEQAKSLANHLTAKLPTGKSYKNTLDLTKP 250
ETSU 658   201  FWHTFINANNATLVITGDMTAEQAKSLANHLTAKLPTGKSYKNTLDLTKP 250
ETSU T-25  201  FWHTFINANNATLVITGDMTAEQAKSLANHLTAKLPTGKSYKNTLDLTKP 250
M-12       201  FWHTFINANNATLVITGDMTAEQAKSLANHLTAKLPTGKSYKNTLDLTKP 250
                **************************************************

ETSU C-2   251  VKARHIHIPHNSSQTQIIIGHPTSKVRTDKAGRQEFSDFSLGNEILAGGD 300
ETSU 658   251  VKARHIHIPHNSSQTQIIIGHPTSKVRTDKAGRQEFSDFSLGNEILAGGD 300
ETSU T-25  251  VKARHIHIPHNSSQTQIIIGHPTSKVRTDKAGRQEFSDFSLGNEILAGGD 300
M-12       251  VKARHIHIPHNSSQTQIIIGHPTSKVRTDKAGRQEFSDFSLGNEILAGGD 300
                **************************************************

ETSU C-2   301  FNARLMKTIREQKGYTYGIYGGMERLRAGGNYVVEFSTDGDKAADAILET 350
ETSU 658   301  FNARLMKTIREQKGYTYGIYGGMERLRAGGNYVVEFSTDGDKAADAILET 350
ETSU T-25  301  FNARLMKTIREQKGYTYGIYGGMERLRAGGNYVVEFSTDGDKAADAILET 350
M-12       301  FNARLMKTIREQKGYTYGIYGGMERLRAGGNYVVEFSTDGDKAADAILET 350
                **************************************************

ETSU C-2   351  LHIINESLNEGITQEELELVRLGNKNGFANIFSSNASIHRVIGALFVADY 400
ETSU 658   351  LHIINESLNEGITQEELELVRLGNKNGFANIFSSNASIHRVIGALFVADY 400
ETSU T-25  351  LHIINESLNEGITQEELELVRLGNKNGFANIFSSNASIHRVIGALFVADY 400
M-12       351  LHIINESLNEGITQEELELVRLGNKNGFANIFSSNASIHRVIGALFVADY 400
                **************************************************

ETSU C-2   401  PKDHLNHTLNRLDNATINSVNTALNLRIKPDEF 433
ETSU 658   401  PKDHLNHTLNRLDNATINSVNTALNLRIKPDEF 433
ETSU T-25  401  PKDHLNHTLNRLDNATINSVNTALNLRIKPDEF 433
M-12       401  PKDHLNHTLNRLDNATINSVNTALNLRIKPDEF 433
                *********************************
```

MORAXELLA (BRANHAMELLA) CATARRHALIS ANTIGENS

RELATED PATENT APPLICATIONS

This application claims the benefit of U.S. Provisional Application Ser. No. 60/290,653, filed May 15, 2001, which is hereby incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 484112_425USPC_SEQUENCE_LISTING.txt. The text file is 46 KB, was created on Oct. 10, 2007, and is being submitted electronically via EFS-Web.

FIELD OF THE INVENTION

The present invention is related to polypeptides, more particularly polypeptides of *Moraxella (Branhamella) catarrhalis* which may be used to prevent, diagnose and/or treat *Moraxella (Branhamella) catarrhalis* infection.

BACKGROUND OF THE INVENTION

*Moraxella (Branhamella) catarrhalis* is a Gram-negative *diplococcus* that causes respiratory tract infections in humans. *M. catarrhalis* is now accepted as the third most common cause of otitis media in infants and children, after *Streptococcus pneumoniae* and *Haemophilus influenzae*. *M. catarrhalis* has also been associated with several other types of infection, including sinusitis, persistent cough, acute laryngitis in adults, suppurative keratitis, conjunctivitis neonatorum, and invasive diseases in the immunocompromised host.

Since approximately 90% of *M. catarrhalis* strains are resistant to antibiotics (β-lactamase positive) and that recurrent otitis media is associated with high morbidity, there is a need for the development of a vaccine that will protect hosts from *M. catarrhalis* infection. An infection by *M. catarrhalis* induces an immune response against antigens found at the surface of the bacterial cells. However, many of these surface proteins are still not characterized, nor has the immune response resulting in protection from infection by different strains been determined.

To develop a vaccine that will protect hosts from *M. catarrhalis* infection, efforts have mainly been concentrated on outer membrane proteins such as the high-molecular-mass protein named ubiquitous surface protein A (UspA). This protein is considered a promising vaccine candidate because a monoclonal antibody and polyclonal antibodies were both shown to be bactericidal and protective in the murine pulmonary-clearance model. However, this protein was shown to be highly variable among the different strains of *M. catarrhalis*. In addition to this protein, other *M. catarrhalis* proteins have generated interest as potential vaccine candidates. The transferrin-binding protein which possesses conserved epitopes exposed on the bacterial surface. However, there was divergence in the degree of antibody cross-reactivity with the protein from one strain to another. Other investigators have also focused on the 45-kDa protein CD (OMP CD). This protein is highly conserved among strains of *M. catarrhalis*, however adults with chronic obstructive pulmonary disease show variability in the immune response against the OMP CD.

Therefore there remains an unmet need for *M. catarrhalis* polypeptides which may be used to prevent, diagnose and/or treat *Moraxella (Branhamella) catarrhalis* infection.

SUMMARY OF THE INVENTION

According to one aspect, the present invention provides an isolated polynucleotide encoding a polypeptide having at least 70% identity to a second polypeptide comprising a sequence chosen from SEQ ID Nos: 2, 4, 6, 8, 10, 12, 14 or fragments or analogs thereof.

According to one aspect, the present invention relates to polypeptides comprising a sequence chosen from SEQ ID No: 2, 4, 6, 8, 10, 12, 14 or fragments or analogs thereof.

In other aspects, there are provided polypeptides encoded by polynucleotides of the invention, pharmaceutical compositions, vectors comprising polynucleotides of the invention operably linked to an expression control region, as well as host cells transfected with said vectors and processes for producing polypeptides comprising culturing said host cells under conditions suitable for expression.

BRIEF DESCRIPTION OF THE DRAWINGS

FIG. 1 represents the DNA sequence of BVH-MC2 gene from *M. catarrhalis* strain ETSU C-2; SEQ ID NO: 1. The underlined portion of the sequence represents the region coding for the leader peptide.

FIG. 2 represents the amino acid sequence of BVH-MC2 polypeptide from *M. catarrhalis* strain ETSU C-2; SEQ ID NO: 2. The underline sequence represents the 30 amino acid residues leader peptide.

FIG. 3 represents the partial DNA sequence of BVH-MC2 gene from *M. catarrhalis* strain ETSU 658; SEQ ID NO: 3.

FIG. 4 represents the partial amino acid sequence of BVH-MC2 polypeptide from *M. catarrhalis* strain ETSU 658; SEQ ID NO: 4.

FIG. 5 represents the partial DNA sequence of BVH-MC2 gene from *M. catarrhalis* strain ETSU T-25; SEQ ID NO: 5.

FIG. 6 represents the partial amino acid sequence of BVH-MC2 polypeptide from *M. catarrhalis* strain ETSU T-25; SEQ ID NO: 6.

FIG. 7 represents the partial DNA sequence of BVH-MC2 gene from *M. catarrhalis* strain M-12; SEQ ID NO: 7.

FIG. 8 represents the partial amino acid sequence of BVH-MC2 polypeptide from *M. catarrhalis* strain M-12; SEQ ID NO: 8.

FIG. 9 represents the DNA sequence of BVH-MC3 gene from *M. catarrhalis* strain ETSU C-2; SEQ ID NO: 9. The underlined portion of the sequence represents the region coding for the leader peptide.

FIG. 10 represents the amino acid sequence of BVH-MC3 polypeptide from *M. catarrhalis* strain ETSU C-2; SEQ ID NO: 10. The underline sequence represents the 46 amino acid residues leader peptide.

FIG. 11 represents the DNA sequence of BVH-MC4 gene from *M. catarrhalis* strain ETSU C-2; SEQ ID NO: 11. The underlined portion of the sequence represents the region coding for the leader peptide.

FIG. 12 represents the amino acid sequence of BVH-MC4 polypeptide *M. catarrhalis* strain ETSU C-2; SEQ ID NO: 12. The underline sequence represents the 42 amino acid residues leader peptide.

FIG. 13 represents the DNA sequence of BVH-MC5 gene from *M. catarrhalis* strain ETSU C-2; SEQ ID NO: 13. The underlined portion of the sequence represents the region coding for the leader peptide.

FIG. 14 represents the amino acid sequence of BVH-MC5 polypeptide *M. catarrhalis* strain ETSU C-2; SEQ ID NO: 14. The underline sequence represents the 60 amino acid residues leader peptide.

FIG. 15 depicts the comparison of the partial nucleotide sequences (SEQ ID NO:35, 3, 5 and 7) of the BVH-MC2 genes from ETSU C-2, ETSU 658, ETSU T-25, and M-12 *M. catarrhalis* strains, respectively, by using the program Clustal W from MacVector sequence analysis software (version 6.5). Underneath the alignment, there is a consensus line where * and blank spaces respectively represent identical nucleotides and differences between sequences.

FIG. 16 depicts the comparison of the predicted amino acid sequences (SEQ ID NO:36, 4, 6, and 8) of the BVH-MC2 partial open reading frames from ETSU C-2, ETSU 658, ETSU T-25, and M-12 *M. catarrhalis* strains, respectively, by using the program Clustal W from MacVector sequence analysis software (version 6.5). Underneath the alignment, there is a consensus line where * characters represent identical amino acid residues.

DETAILED DESCRIPTION OF THE INVENTION

The present invention provides purified and isolated polynucleotides, which encode *Moraxella* polypeptides which may be used to prevent, diagnose and/or treat *Moraxella* infection.

According to one aspect, the present invention provides an isolated polynucleotide encoding a polypeptide having at least 70% identity to a second polypeptide comprising a sequence chosen from SEQ ID NO: 2, 4, 6, 8, 10, 12, 14 or fragments or analogs thereof.

According to one aspect, the present invention provides an isolated polynucleotide encoding a polypeptide having at least 80% identity to a second polypeptide comprising a sequence chosen from SEQ ID NO: 2, 4, 6, 8, 10, 12, 14 or fragments or analogs thereof.

According to one aspect, the present invention provides an isolated polynucleotide encoding a polypeptide having at least 95% identity to a second polypeptide comprising a sequence chosen from SEQ ID NO: 2, 4, 6, 8, 10, 12, 14 or fragments or analogs thereof.

According to one aspect, the present invention provides an isolated polynucleotide encoding a polypeptide having at least 70% identity to a second polypeptide comprising a sequence chosen from SEQ ID NO: 2, 4, 6, 8, 10, 12 or 14.

According to one aspect, the present invention provides an isolated polynucleotide encoding a polypeptide having at least 80% identity to a second polypeptide comprising a sequence chosen from SEQ ID NO: 2, 4, 6, 8, 10, 12 or 14.

According to one aspect, the present invention provides an isolated polynucleotide encoding a polypeptide having at least 95% identity to a second polypeptide comprising a sequence chosen from SEQ ID NO: 2, 4, 6, 8, 10, 12 or 14.

According to one aspect, the present invention relates to polypeptides comprising a sequence chosen from SEQ ID Nos: 2, 4, 6, 8, 10, 12, 14 or fragments or analogs thereof.

According to one aspect, the present invention relates to polypeptides characterized by the amino acid sequence comprising SEQ ID NO: 2, 4, 6, 8, 10, 12 or 14.

According to one aspect, the present invention provides a polynucleotide encoding an epitope bearing portion of a polypeptide comprising a sequence chosen from SEQ ID NO: 2, 4, 6, 8, 10, 12, 14 or fragments or analogs thereof.

According to one aspect, the present invention provides a polynucleotide encoding an epitope bearing portion of a polypeptide comprising a sequence chosen from SEQ ID NO: 2, 4, 6, 8, 10, 12 or 14.

According to one aspect, the present invention relates to epitope bearing portions of a polypeptide comprising a sequence chosen from SEQ ID NO: 2, 4, 6, 8, 10, 12, 14 or fragments or analogs thereof.

According to one aspect, the present invention relates to epitope bearing portions of a polypeptide comprising a sequence chosen from SEQ ID NO: 2, 4, 6, 8, 10, 12 or 14.

According to one aspect, the present invention provides an isolated polynucleotide encoding a polypeptide having at least 70% identity to a second polypeptide comprising a sequence chosen from SEQ ID NO: 2, 4, 6, 8, 10, 12 or 14.

According to one aspect, the present invention provides an isolated polynucleotide encoding a polypeptide having at least 80% identity to a second polypeptide comprising a sequence chosen from SEQ ID NO: 2, 4, 6, 8, 10, 12 or 14.

According to one aspect, the present invention provides an isolated polynucleotide encoding a polypeptide having at least 90% identity to a second polypeptide comprising a sequence chosen from SEQ ID NO: 2, 4, 6, 8, 10, 12 or 14.

According to one aspect, the present invention provides an isolated polynucleotide encoding a polypeptide having at least 95% identity to a second polypeptide comprising a sequence chosen from SEQ ID NO: 2, 4, 6, 8, 10, 12 or 14.

According to one aspect, the present invention relates to polypeptides comprising a sequence chosen from SEQ ID No: 2, 4, 6, 8, 10, 12 or 14.

According to one aspect, the present invention provides an isolated polynucleotide comprising a polynucleotide chosen from:

(a) a polynucleotide encoding a polypeptide having at least 70% identity to a second polypeptide comprising a sequence chosen from: SEQ ID NO: 2, 4, 6, 8, 10, 12, 14 or fragments or analogs thereof;

(b) a polynucleotide encoding a polypeptide having at least 80% identity to a second polypeptide comprising a sequence chosen from: SEQ ID NO: 2, 4, 6, 8, 10, 12, 14 or fragments or analogs thereof;

(c) a polynucleotide encoding a polypeptide having at least 95% identity to a second polypeptide comprising a sequence chosen from: SEQ ID NO: 2, 4, 6, 8, 10, 12, 14 or fragments or analogs thereof;

(d) a polynucleotide encoding a polypeptide comprising a sequence chosen from: SEQ ID NO: 2, 4, 6, 8, 10, 12, 14 or fragments or analogs thereof;

(e) a polynucleotide encoding a polypeptide capable of generating antibodies having binding specificity for a polypeptide comprising a sequence chosen from: SEQ ID NO: 2, 4, 6, 8, 10, 12, 14 or fragments or analogs thereof;

(f) a polynucleotide encoding an epitope bearing portion of a polypeptide comprising a sequence chosen from SEQ ID NO: 2, 4, 6, 8, 10, 12, 14 or fragments or analogs thereof;

(g) a polynucleotide comprising a sequence chosen from SEQ ID NO: 1, 3, 5, 7, 9, 11, 13 or fragments or analogs thereof;

(h) a polynucleotide that is complementary to a polynucleotide in (a), (b), (c), (d), (e), (f) or (g).

According to one aspect, the present invention provides an isolated polynucleotide comprising a polynucleotide chosen from:

(a) a polynucleotide encoding a polypeptide having at least 70% identity to a second polypeptide comprising a sequence chosen from: SEQ ID NO: 2, 4, 6, 8, 10, 12 or 14;

(b) a polynucleotide encoding a polypeptide having at least 80% identity to a second polypeptide comprising a sequence chosen from: SEQ ID NO: 2, 4, 6, 8, 10, 12 or 14;

(c) a polynucleotide encoding a polypeptide having at least 95% identity to a second polypeptide comprising a sequence chosen from: SEQ ID NO: 2, 4, 6, 8, 10, 12 or 14;

(d) a polynucleotide encoding a polypeptide comprising a sequence chosen from: SEQ ID NO: 2, 4, 6, 8, 10, 12 or 14;

(e) a polynucleotide encoding a polypeptide capable of raising antibodies having binding specificity for a polypeptide comprising a sequence chosen from: SEQ ID NO: 2, 4, 6, 8, 10, 12 or 14;

(f) a polynucleotide encoding an epitope bearing portion of a polypeptide comprising a sequence chosen from SEQ ID NO: 2, 4, 6, 8, 10, 12 or 14;

(g) a polynucleotide comprising a sequence chosen from SEQ ID NO: 1, 3, 5, 7, 9, 11 and 13;

(h) a polynucleotide that is complementary to a polynucleotide in (a), (b), (c), (d), (e), (f) or (g).

According to one aspect, the present invention provides an isolated polypeptide comprising a polypeptide chosen from:

(a) a polypeptide having at least 70% identity to a second polypeptide comprising a sequence chosen from SEQ ID NO: 2, 4, 6, 8, 10, 12, 14 or fragments or analogs thereof;

(b) a polypeptide having at least 80% identity to a second polypeptide comprising a sequence chosen from SEQ ID NO: 2, 4, 6, 8, 10, 12, 14 or fragments or analogs thereof;

(c) a polypeptide having at least 95% identity to a second polypeptide comprising a sequence chosen from SEQ ID NO: 2, 4, 6, 8, 10, 12, 14 or fragments or analogs thereof;

(d) a polypeptide comprising a sequence chosen from SEQ ID NO: 2, 4, 6, 8, 10, 12, 14 or fragments or analogs thereof;

(e) a polypeptide capable of raising antibodies having binding specificity for a polypeptide comprising a sequence chosen from SEQ ID NO: 2, 4, 6, 8, 10, 12, 14 or fragments or analogs thereof;

(f) an epitope bearing portion of a polypeptide comprising a sequence chosen from SEQ ID NO: 2, 4, 6, 8, 10, 12, 14 or fragments or analogs thereof;

(g) the polypeptide of (a), (b), (c), (d), (e) or (f) wherein the N-terminal Met residue is deleted;

(h) the polypeptide of (a), (b), (c), (d), (e) or (f) wherein the secretory amino acid sequence is deleted.

According to one aspect, the present invention provides an isolated polypeptide comprising a polypeptide chosen from:

(a) a polypeptide having at least 70% identity to a second polypeptide comprising a sequence chosen from SEQ ID NO: 2, 4, 6, 8, 10, 12 or 14;

(b) a polypeptide having at least 80% identity to a second polypeptide comprising a sequence chosen from SEQ ID NO: 2, 4, 6, 8, 10, 12 or 14;

(c) a polypeptide having at least 95% identity to a second polypeptide comprising a sequence chosen from SEQ ID NO: 2, 4, 6, 8, 10, 12 or 14;

(d) a polypeptide comprising a sequence chosen from SEQ ID NO: 2, 4, 6, 8, 10, 12 or 14;

(e) a polypeptide capable of raising antibodies having binding specificity for a polypeptide comprising a sequence chosen from SEQ ID NO: 2, 4, 6, 8, 10, 12 or 14;

(f) an epitope bearing portion of a polypeptide comprising a sequence chosen from SEQ ID NO: 2, 4, 6, 8, 10, 12 or 14;

(g) the polypeptide of (a), (b), (c), (d), (e) or (f) wherein the N-terminal Met residue is deleted;

(h) the polypeptide of (a), (b), (c), (d), (e) or (f) wherein the secretory amino acid sequence is deleted.

Those skilled in the art will appreciate that the invention includes DNA molecules, i.e. polynucleotides and their complementary sequences that encode analogs such as mutants, variants, homologues and derivatives of such polypeptides, as described herein in the present patent application. The invention also includes RNA molecules corresponding to the DNA molecules of the invention. In addition to the DNA and RNA molecules, the invention includes the corresponding polypeptides and monospecific antibodies that specifically bind to such polypeptides.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in a host.

In a further embodiment, the present invention also relates to polypeptides which are able to raise antibodies having binding specificity to the polypeptides of the present invention as defined above.

An antibody that "has binding specificity" is an antibody that recognizes and binds the selected polypeptide but which does not substantially recognize and bind other molecules in a sample, e.g., a biological sample, which naturally includes the selected peptide. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

In an additional aspect of the invention there are provided antigenic/immunogenic fragments of the polypeptides of the invention, or of analogs thereof.

The fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a polypeptide or analog thereof as described herein. The present invention further provides fragments having at least 10 contiguous amino acid residues from the polypeptide sequences of the present invention. In one embodiment, at least 15 contiguous amino acid residues. In one embodiment, at least 20 contiguous amino acid residues.

The skilled person will appreciate that analogs of the polypeptides of the invention will also find use in the context of the present invention, i.e. as antigenic/immunogenic material. Thus, for instance proteins or polypeptides which include one or more additions, deletions, substitutions or the like are encompassed by the present invention.

As used herein, "fragments", "analogs" or "derivatives" of the polypeptides of the invention include those polypeptides in which one or more of the amino acid residues are substituted with a conserved or non-conserved amino acid residue (preferably conserved) and which may be natural or unnatural. In one embodiment, derivatives and analogs of polypeptides of the invention will have about 80% identity with those sequences illustrated in the figures or fragments thereof. That is, 80% of the residues are the same. In a further embodiment, polypeptides will have greater than 80% identity. In a further embodiment, polypeptides will have greater than 85% identity. In a further embodiment, polypeptides will have greater than 90% identity. In a further embodiment, polypeptides will have greater than 95% identity. In a further embodiment, polypeptides will have greater than 99% identity. In a further embodiment, analogs of polypeptides of the invention will have fewer than about 20 amino acid residue substitutions, modifications or deletions and more preferably less than 10.

These substitutions are those having a minimal influence on the secondary structure and hydropathic nature of the polypeptide. Preferred substitutions are those known in the art as conserved, i.e. the substituted residues share physical or chemical properties such as hydrophobicity, size, charge or functional groups. These include substitutions such as those described by Dayhoff, M. in Atlas of Protein Sequence and Structure 5, 1978 and by Argos, P. in EMBO J. 8, 779-785, 1989. For example, amino acids, either natural or unnatural, belonging to one of the following groups represent conservative changes:

```
ala, pro, gly, gln, asn, ser, thr, val;

cys, ser, tyr, thr;

val, ile, leu, met, ala, phe;

lys, arg, orn, his; and phe, tyr, trp, his.
```

The preferred substitutions also include substitutions of D-enantiomers for the corresponding L-amino acids.

In an alternative approach, the analogs could be fusion polypeptides, incorporating moieties which render purification easier, for example by effectively tagging the desired polypeptide. It may be necessary to remove the "tag" or it may be the case that the fusion polypeptide itself retains sufficient antigenicity to be useful.

The percentage of homology is defined as the sum of the percentage of identity plus the percentage of similarity or conservation of amino acid type.

In one embodiment, analogs of polypeptides of the invention will have about 70% identity with those sequences illustrated in the figures or fragments thereof. That is, 70% of the residues are the same. In a further embodiment, polypeptides will have greater than 80% identity. In a further embodiment, polypeptides will have greater than 85% identity. In a further embodiment, polypeptides will have greater than 90% identity. In a further embodiment, polypeptides will have greater than 95% identity. In a further embodiment, polypeptides will have greater than 99% identity. In a further embodiment, analogs of polypeptides of the invention will have fewer than about 20 amino acid residue substitutions, modifications or deletions and more preferably less than 10.

In one embodiment, analogs of polypeptides of the invention will have about 70% homology with those sequences illustrated in the figures or fragments thereof. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, analogs of polypeptides of the invention will have fewer than about 20 amino acid residue substitutions, modifications or deletions and more preferably less than 10.

One can use a program such as the CLUSTAL program to compare amino acid sequences. This program compares amino acid sequences and finds the optimal alignment by inserting spaces in either sequence as appropriate. It is possible to calculate amino acid identity or homology for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In an alternative approach, the analogs or derivatives could be fusion polypeptides, incorporating moieties which render purification easier, for example by effectively tagging the desired protein or polypeptide, it may be necessary to remove the "tag" or it may be the case that the fusion polypeptide itself retains sufficient antigenicity to be useful.

It is well known that it is possible to screen an antigenic polypeptide to identify epitopic regions, i.e. those regions which are responsible for the polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties.

Thus, for fragments according to the present invention the degree of identity is perhaps irrelevant, since they may be 100% identical to a particular part of a polypeptide, analog as described herein.

Thus, what is important for analogs, derivatives and fragments is that they possess at least a degree of the antigenicity/immunogenicity of the protein or polypeptide from which they are derived.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *Moraxella* strains.

Moreover, the polypeptides of the present invention can be modified by terminal —$NH_2$ acylation (eg. by acetylation, or thioglycolic acid amidation, terminal carboxy amidation, e.g. with ammonia or methylamine) to provide stability, increased hydrophobicity for linking or binding to a support or other molecule.

Also contemplated are hetero and homo polypeptide multimers of the polypeptide fragments and analogues. These polymeric forms include, for example, one or more polypeptides that have been cross-linked with cross-linkers such as avidin/biotin, gluteraldehyde or dimethyl-superimidate. Such polymeric forms also include polypeptides containing two or more tandem or inverted contiguous sequences, produced from multicistronic mRNAs generated by recombinant DNA technology.

In a further embodiment, the present invention also relates to chimeric polypeptides which comprise one or more polypeptides or fragments or analogs thereof as defined in the figures of the present application.

In a further embodiment, the present invention also relates to chimeric polypeptides comprising two or more polypeptides having a sequence chosen from SEQ ID NO: 2, 4, 6, 8, 10, 12, 14 or fragments or analogs thereof; provided that the polypeptides are linked as to formed a chimeric polypeptide.

In a further embodiment, the present invention also relates to chimeric polypeptides comprising two or more polypeptides comprising a sequence chosen from SEQ ID NO: 2, 4, 6, 8, 10, 12 or 14 provided that the polypeptides are linked as to formed a chimeric polypeptide.

Preferably, a fragment, analog or derivative of a polypeptide of the invention will comprise at least one antigenic region i.e. at least one epitope.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different polypeptides may be a single bond or may be composed of a linking group of at least two, typically at least four, and not more than 16, but usually not more than about 14 carbon atoms.

In a particular embodiment, polypeptide fragments and analogs of the invention do not contain a starting residue, such as methionine (Met) or valine (Val). Preferably, polypeptides will not incorporate a leader or secretory sequence (signal sequence). The signal portion of a polypeptide of the invention may be determined according to established molecular biological techniques. In general, the polypeptide of interest may be isolated from a *Moraxella* culture and subsequently sequenced to determine the initial residue of the mature protein and therefore the sequence of the mature polypeptide.

It is understood that polypeptides can be produced and/or used without their start codon (methionine or valine) and/or without their leader peptide to favor production and purification of recombinant polypeptides. It is known that cloning genes without sequences encoding leader peptides will restrict the polypeptides to the cytoplasm of *E. coli* and will facilitate their recovery (Glick, B. R. and Pasternak, J. J. (1998) Manipulation of gene expression in prokaryotes. In "Molecular biotechnology: Principles and applications of recombinant DNA", 2nd edition, ASM Press, Washington D.C., p.109-143).

According to another aspect of the invention, there are also provided (i) a composition of matter containing a polypeptide of the invention, together with a carrier, diluent or adjuvant; (ii) a pharmaceutical composition comprising a polypeptide of the invention and a carrier, diluent or adjuvant; (iii) a vaccine comprising a polypeptide of the invention and a carrier, diluent or adjuvant; (iv) a method for inducing an immune response against *Moraxella*, in a host, by administering to the host, an immunogenically effective amount of a polypeptide of the invention to elicit an immune response, e.g., a protective immune response to *Moraxella*; and particularly, (v) a method for preventing and/or treating a *Moraxella* infection, by administering a prophylactic or therapeutic amount of a polypeptide of the invention to a host in need.

According to another aspect of the invention, there are also provided (i) a composition of matter containing a polynucleotide of the invention, together with a carrier, diluent or adjuvant; (ii) a pharmaceutical composition comprising a polynucleotide of the invention and a carrier, diluent or adjuvant; (iii) a method for inducing an immune response against *Moraxella*, in a host, by administering to the host, an immunogenically effective amount of a polynucleotide of the invention to elicit an immune response, e.g., a protective immune response to *Moraxella*; and particularly, (iv) a method for preventing and/or treating a *Moraxella* infection, by administering a prophylactic or therapeutic amount of a polynucleotide of the invention to a host in need. Before immunization, the polypeptides of the invention can also be coupled or conjugated to carrier proteins such as tetanus toxin, diphtheria toxin, hepatitis B virus surface antigen, poliomyelitis virus VP1 antigen or any other viral or bacterial toxin or antigen or any suitable proteins to stimulate the development of a stronger immune response. This coupling or conjugation can be done chemically or genetically. A more detailed description of peptide-carrier conjugation is available in Van Regenmortel, M. H. V., Briand J. P., Muller S., Plaué S., <<Synthetic Polypeptides as antigens>> in Laboratory Techniques in Biochemistry and Molecular Biology, Vol.19 (ed.) Burdou, R. H. & Van Knippenberg P. H. (1988), Elsevier New York.

According to another aspect, there are provided pharmaceutical compositions comprising one or more *Moraxella* polypeptides of the invention in a mixture with a pharmaceutically acceptable adjuvant. Suitable adjuvants include (1) oil-in-water emulsion formulations such as MF59™, SAF™, Ribi™; (2) Freund's complete or incomplete adjuvant; (3) salts i.e. $AlK(SO_4)_2$, $AlNa(SO_4)_2$, $AlNH_4(SO_4)_2$, $Al(OH)_3$, $AlPO_4$, silica, kaolin; (4) saponin derivatives such as Stimulon™ or particles generated therefrom such as ISCOMs (immunostimulating complexes); (5) cytokines such as interleukins, interferons, macrophage colony stimulating factor (M-CSF), tumor necrosis factor (TNF); (6) other substances such as carbon polynucleotides i.e. poly IC and poly AU, detoxified cholera toxin (CTB) and *E. coli* heat labile toxin for induction of mucosal immunity. A more detailed description of adjuvant is available in a review by M. Z. I Khan et al. in Pharmaceutical Research, vol. 11, No. 1 (1994) pp2-11, and also in another review by Gupta et al., in Vaccine, Vol. 13, No. 14, pp1263-1276 (1995) and in WO 99/24578. Preferred adjuvants include QuilA™, QS21™, Alhydrogel™ and Adjuphos™.

Pharmaceutical compositions of the invention may be administered parenterally by injection, rapid infusion, nasopharyngeal absorption, dermoabsorption, or buccal or oral.

Pharmaceutical compositions of the invention are used for the prophylaxis of *Moraxella* infection and/or diseases and symptoms mediated by *Moraxella* infection as described in Manual of Clinical Microbiology, P. R. Murray (Ed, in chief), E. J. Baron, M. A. Pfaller, F. C. Tenover and R. H. Yolken. ASM Press, Washington, D.C. seventh edition, 1999, 1773p. In one embodiment, pharmaceutical compositions of the present invention are used for the treatment or prophylaxis of otitis media, sinusitis, persistent cough, acute laryngitis, suppurative keratitis, conjunctivitis neonatorum. In one embodiment, vaccine compositions of the invention are used for the treatment or prophylaxis of *Moraxella* infection and/or diseases and symptoms mediated by *Moraxella* infection. In a further embodiment, the *Moraxella* infection is *Moraxella catarrhalis*.

In a further embodiment, the invention provides a method for prophylaxis or treatment of *Moraxella* infection in a host susceptible to *Moraxella* infection comprising administering to said host a prophylactic or therapeutic amount of a composition of the invention.

As used in the present application, the term "host" includes mammals. In a further embodiment, the mammal is human.

In a particular embodiment, pharmaceutical compositions are administered to those hosts at risk of *Moraxella* infection such as neonates, infants, children, elderly and immunocompromised hosts.

In a particular embodiment, pharmaceutical compositions are administered to those hosts at risk of *Moraxella* infection such as adults.

Pharmaceutical compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

Pharmaceutical compositions are preferably in unit dosage form of about 0.1 µg to 10 mg and more preferably 1 g to 1 mg and most preferably 10 to 100 µg 1 to 3 times with an interval of about 1 to 6 week intervals between immunizations.

According to another aspect, there are provided polynucleotides encoding polypeptides characterized by the amino acid sequence comprising a sequence chosen from SEQ ID NO: 2, 4, 6, 8, 10, 12, 14 or fragments or analogs thereof.

In one embodiment, polynucleotides are those illustrated in SEQ ID No: 1, 3, 5, 7, 9, 11, 13 which may include the open reading frames (ORF), encoding the polypeptides of the invention.

It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 70% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity.

Suitable stringent conditions for hybridation can be readily determined by one of skilled in the art (see for example Sambrook et al., (1989) Molecular cloning: A Laboratory Manual, $2^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridize under stringent conditions to either (a) a DNA sequence encoding a polypeptide or (b) the complement of a DNA sequence encoding a polypeptide;

wherein said polypeptide comprises a sequence chosen from SEQ ID NO: 2, 4, 6, 8, 10, 12 or 14 or fragments or analogs thereof.

In a further embodiment, the present invention provides polynucleotides that hybridize under stringent conditions to either (a) a DNA sequence encoding a polypeptide or (b) the complement of a DNA sequence encoding a polypeptide;

wherein said polypeptide comprises a sequence chosen from SEQ ID NO: 2, 4, 6, 8, 10, 12 or 14.

In a further embodiment, the present invention provides polynucleotides that hybridize under stringent conditions to either (a) a DNA sequence encoding a polypeptide or (b) the complement of a DNA sequence encoding a polypeptide;

wherein said polypeptide comprises at least 10 contiguous amino acid residues from a polypeptide comprising a sequence chosen from SEQ ID NO: 2, 4, 6, 8, 10, 12 or 14 or fragments or analogs thereof.

In a further embodiment, the present invention provides polynucleotides that hybridize under stringent conditions to either (a) a DNA sequence encoding a polypeptide or (b) the complement of a DNA sequence encoding a polypeptide;

wherein said polypeptide comprises at least 10 contiguous amino acid residues from a polypeptide comprising a sequence chosen from SEQ ID NO: 2, 4, 6, 8, 10, 12 or 14.

In a further embodiment, polynucleotides are those illustrated in SEQ ID NO: 1, 3, 5, 7, 9, 11, 13 or fragments or analogs thereof encoding polypeptides of the invention.

In a further embodiment, polynucleotides are those illustrated in SEQ ID NO: 1, 3, 5, 7, 9, 11 or 13 encoding polypeptides of the invention.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation)

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K.; Springer-verlag, New York, 3rd Edition, 1993, 380 pages; Current Protocols in Immunology, Edited by Coligan J. E. et al., John Wiley & Sons Inc., New York.

The present invention provides a process for producing a polypeptide comprising culturing a host cell of the invention under conditions suitable for expression of said polypeptide.

For recombinant production, host cells are transfected with vectors which encode the polypeptides of the invention, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York). Suitable promoters include but are not limited to LTR or SV40 promoter, *E. coli* lac, tac or trp promoters and the phage lambda PL promoter. Vectors will preferably incorporate an origin of replication as well as selection markers i.e. ampicilin resistance gene. Suitable bacterial vectors include pET, pQE70, pQE60, pQE-9, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and pSVL. Host cells may be bacterial i.e. *E. coli, Bacillus subtilis, Streptomyces*; fungal i.e. *Aspergillus niger, Aspergillus nidulins*; yeast i.e. *Saccharomyces* or eukaryotic i.e. CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptides may be expressed with or without a leader or secretion sequence. In the former case the leader may be removed using post-translational processing (see U.S. Pat. No. 4,431,739; U.S. Pat. No. 4,425,437; and U.S. Pat. No. 4,338,397) or be chemically removed subsequent to purifying the expressed polypeptide.

According to a further aspect, the *Moraxella* polypeptides of the invention may be used in a diagnostic test for *Moraxella* infection, in particular *Moraxella catarrhalis* infection. Several diagnostic methods are possible, for example detecting *Moraxella* organism in a biological sample, the following procedure may be followed:

a) obtaining a biological sample from a host;
b) incubating an antibody or fragment thereof reactive with a *Moraxella* polypeptide of the invention with the biological sample to form a mixture; and
c) detecting specifically bound antibody or bound fragment in the mixture which indicates the presence of *Moraxella*.

Alternatively, a method for the detection of antibody specific to a *Moraxella* antigen in a biological sample containing or suspected of containing said antibody may be performed as follows:

a) obtaining a biological sample from a host;
b) incubating one or more *Moraxella* polypeptides of the invention or fragments thereof with the biological sample to form a mixture; and
c) detecting specifically bound antigen or bound fragment in the mixture which indicates the presence of antibody specific to *Moraxella*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the protein are present in an organism.

The DNA sequences encoding polypeptides of the invention may also be used to design DNA probes for use in detecting the presence of *Moraxella* in a biological sample suspected of containing such bacteria. The detection method of this invention comprises:

a) obtaining the biological sample from a host;
b) incubating one or more DNA probes having a DNA sequence encoding a polypeptide of the invention or fragments thereof with the biological sample to form a mixture; and
c) detecting specifically bound DNA probe in the mixture which indicates the presence of *Moraxella* bacteria.

The DNA probes of this invention may also be used for detecting circulating *Moraxella* i.e. *Moraxella* nucleic acids in a sample, for example using a polymerase chain reaction, as a method of diagnosing *Moraxella* infections. The probe may be synthesized using conventional techniques and may be immobilized on a solid phase, or may be labelled with a detectable label. A preferred DNA probe for this application is an oligomer having a sequence complementary to at least about 6 contiguous nucleotides of the *Moraxella* polypeptides of the invention. In a further embodiment, the preferred DNA probe will be an oligomer having a sequence complementary to at least about 15 contiguous nucleotides of the *Moraxella* polypeptides of the invention. In a further embodiment, the preferred DNA probe will be an oligomer having a sequence complementary to at least about 30 contiguous nucleotides of the *Moraxella* polypeptides of the invention. In a further embodiment, the preferred DNA probe will be an oligomer having a sequence complementary to at least about 50 contiguous nucleotides of the *Moraxella* polypeptides of the invention.

Another diagnostic method for the detection of *Moraxella* in a host comprises:

a) labelling an antibody reactive with a polypeptide of the invention or fragment thereof with a detectable label;
b) administering the labelled antibody or labelled fragment to the host; and
c) detecting specifically bound labelled antibody or labelled fragment in the host which indicates the presence of *Moraxella*.

Alternatively, a method for the detection of antibody specific to a *Moraxella* antigen in a biological sample containing or suspected of containing said antibody may be performed as follows:

a) obtaining a biological sample from a host;
b) incubating one or more *Moraxella* polypeptides of the invention or fragments thereof with the biological sample to form a mixture; and
c) detecting specifically bound antigen or bound fragment in the mixture which indicates the presence of antibody specific to *Moraxella*.

One of skill in the art will recognize that the diagnostic test may take several forms, including an immunological test such as an enzyme-linked immunosorbent assay (ELISA), a radioimmunoassay or a latex agglutination assay, essentially to determine whether antibodies specific for the protein are present in an organism.

The DNA sequences encoding polypeptides of the invention may also be used to design DNA probes for use in detecting the presence of *Moraxella* in a biological sample suspected of containing such bacteria. The detection method of this invention comprises:

a) obtaining the biological sample from a host;
b) incubating one or more DNA probes having a DNA sequence encoding a polypeptide of the invention or fragments thereof with the biological sample to form a mixture; and c) detecting specifically bound DNA probe in the mixture which indicates the presence of *Moraxella* bacteria.

According to one aspect, the present invention provides the use of an antibody for treatment and/or prophylaxis of *Moraxella* infections.

A further aspect of the invention is the use of the *Moraxella* polypeptides of the invention as immunogens for the production of specific antibodies for the diagnosis and in particular the treatment of *Moraxella* infection. Suitable antibodies may be determined using appropriate screening methods, for example by measuring the ability of a particular antibody to passively protect against *Moraxella* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Moraxella* polypeptides but is preferably specific for one.

According to one aspect, the present invention provides the use of an antibody for prophylaxis and/or treatment of *Moraxella* infections.

A further aspect of the invention is the use of the *Moraxella* polypeptides of the invention as immunogens for the production of specific antibodies for the diagnosis and in particular the treatment of *Moraxella* infection. Suitable antibodies may be determined using appropriate screening methods, for example by measuring the ability of a particular antibody to passively protect against *Moraxella* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Moraxella* polypeptides but is preferably specific for one.

A further aspect of the invention is the use of the antibodies directed to the polypeptides of the invention for passive immunization. One could use the antibodies described in the present application.

A further aspect of the invention is a method for immunization, whereby an antibody raised by a polypeptide of the invention is administered to a host in an amount sufficient to provide a passive immunization.

In a further embodiment, the invention provides the use of a pharmaceutical composition of the invention in the manufacture of a medicament for the prophylactic or therapeutic treatment of *Moraxella* infection.

In a further embodiment, the invention provides a kit comprising a polypeptide of the invention for detection or diagnosis of *Moraxella* infection.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE 1

This example illustrates the cloning and molecular characteristics of BVH-MC2 gene and corresponding polypeptide.

The coding region of *M. catarrhalis* BVH-MC2 (SEQ ID NO: 1) gene was amplified by PCR (DNA Thermal Cycler GeneAmp® PCR system 2400 Perkin Elmer, San Jose, Calif.) from genomic DNA of *M. catarrhalis* strain ETSU C-2 using the following oligos that contained base extensions for the addition of restriction sites NdeI (CATATG) and XhoI (CTCGAG): DMAR544 (5'-CATCAGTGCATATGAATAC-GACACACCATCACACG-3') (SEQ ID NO:15); DMAR545 (5'-GAGTTATTCTCGAGTTTGTCCAAATTTG-GCTTAGTTTTAC-3') (SEQ ID NO:16). PCR products were purified from agarose gel using a QIA® quick gel extraction kit from QIAgen® following the manufacturer's instructions (Chatsworth, Calif.), and digested with NdeI and XhoI (Amersham Pharmacia Biotech, Inc, Baie d'Urfé, Canada). The pET21b(+) vector (Novagen, Madison, Wis.) was digested with NdeI and XhoI and purified from agarose gel using a QIA® quick gel extraction kit from QIAgen® (Chatsworth, Calif.). The NdeI-XhoI PCR products were ligated to the NdeI-XhoI pET21b(+) expression vector. The ligated products were transformed into *E. coli* strain DH5α [φ80dlacZΔM15 Δ(lacZYA-argF)U169 endA1 recA1 hsdR17($r_K^-$–$m_K^+$) deoR thi-1 supE44 λ⁻gyrA96 relA1] (Gibco BRL, Gaithersburg, Md.) according to the method of Simanis (Hanahan, D. DNA Cloning, 1985, D.M. Glover (ed), pp. 109-135). Recombinant pET21b(+) plasmid (rpET21b(+)) containing BVH-MC2 gene was purified using a QIAgen® kit (Chatsworth, Calif.) and DNA insert was sequenced (Taq Dye Deoxy Terminator Cycle Sequencing kit, ABI, Foster City, Calif.).

TABLE 1

Oligonucleotide primers used for PCR amplification of *M. catarrhalis* genes.

| Genes | Primers I.D. | Restriction site | Vector | Sequence |
|---|---|---|---|---|
| BVH-MC2 | DMAR544 | NdeI | pET21b (+) | 5'-CATCAGTGCATATGAATACGACACACCATCACACG-3' (SEQ ID No: 15) |
| BVH-MC2 | DMAR545 | XhoI | pET21b (+) | 5'-GAGTTATTCTCGAGTTTGTCCAAATTTGGCTTAGTTTTAC-3' (SEQ ID No: 16) |

TABLE 1-continued

Oligonucleotide primers used for PCR amplification of *M. catarrhalis* genes.

| Genes | Primers I.D. | Restriction site | Vector | Sequence |
|---|---|---|---|---|
| BVH-MC2 | DMAR544a | BglII | pCMV-GH | 5'-TCAGTGAGATCTTGAATACGACACACCATC-3' (SEQ ID No: 17) |
| BVH-MC2 | DMAR545a | SalI | pCMV-GH | 5'-GATTTGAGTTGTCGACTTATTTGTCCAAATTTG-3' (SEQ ID No: 18) |
| BVH-MC3 | DMAR592 | NdeI | pET21b (+) | 5'-CGGAGTGCCATATGAGCTTAATTAATAAATTAAATG-3' (SEQ ID No: 19) |
| BVH-MC3 | BMAR593 | XhoI | pET21b (+) | 5'-TATAACTCGAGGTTTTGTGCAACAGGTGTTG-3' (SEQ ID No: 20) |
| BVH-MC3 | DMAR592a | BglII | pCMV-GH | 5'-CGCTTGAGATCTTGGAAGATGTGTATCAGCGTGC-3' (SEQ ID No: 21) |
| BVH-MC3 | DMAR593a | HindIII | pCMV-GH | 5'-CAATAACAAAGCTTTCAGTTTTGTGCAACAGGTGTTG-3' (SEQ ID No: 22) |
| BVH-MC4 | RIOS71 | NdeI | pET21b (+) | 5'-AACCGCACATATGTATCGCTTGGTGTCACCACC-3' (SEQ ID No: 23) |
| BVH-MC4 | RIOS72 | XhoI | pET21b (+) | 5'-GGTGACTCGAGGTACTCATCACCAACTAATCGCAC-3' (SEQ ID No: 24) |
| BVH-MC4 | RIOS71a | BamHI | pCMV-GH | 5'-GCAGGATCCTTATCGCTTGGTGTCACC-3' (SEQ ID No: 25) |
| BVH-MC4 | RIOS72a | SalI | pCMV-GH | 5'-ATCAATCGGGTCGACTTAGTACTCATCACCA-3' (SEQ ID No: 26) |
| BVH-MC5 | RIOS59 | NdeI | pET21b (+) | 5'-AAAGCTTCATATGGCCCAAAGTCAAGAATCTGCC-3' (SEQ ID No: 27) |
| BVH-MC5 | RIOS60 | XhoI | pET21b (+) | 5'-CGATAACTCGAGTTGAACATCAGGCACCTGC-3' (SEQ ID No: 28) |
| BVH-MC5 | RIOS59a | BglII | pCMV-GH | 5'-ACCATTCAAAAGAGATCTTGGCCCAAAGTCAAGAATCTG-3' (SEQ ID No: 29) |
| BVH-MC5 | RIOS60a | SalI | pCMV-GH | 5'-GTTAGACCGAGTCGACTCATTGAACATCAGGCA-3' (SEQ ID No: 30) |

It was determined that the open reading frame (ORF) which codes for BVH-MC2 polypeptide contains 1467-bp and encodes a 488 amino acid residues polypeptide with a predicted pI of 6.08 and a predicted molecular mass of 53754.35 Da. Analysis of the predicted amino acid residues sequence (SEQ ID NO: 2) using the Spscan software (Wisconsin Sequence Analysis Package; Genetics Computer Group) suggested the existence of a 30 amino acid residues signal peptide (MDTDMKHLTKHRLSAAIIGVLLFISPS-VQA) (SEQ ID NO:31), which ends with a cleavage site located between an alanine and an asparagine residues.

To confirm the presence by PCR amplification of BVH-MC2 (SEQ ID NO: 1) gene, the following 4 distinct *M. catarrhalis* strains were used: *M. catarrhalis* ETSU C-2, ETSU T-25, and ETSU 658 clinical isolates were provided by the East Tennessee State University; *M. catarrhalis* strain M-12 was provided by the centre de recherche en infectiologie du centre hospitalier de l'université Laval. The *E. coli* XL1-Blue MRF' was used in these experiments as negative control. BVH-MC2 (SEQ ID NO: 1) gene was amplified by PCR (DNA Thermal Cycler GeneAmp PCR system 2400 Perkin Elmer, San Jose, Calif.) from genomic DNA from the 4 *M. catarrhalis* strains, and the control *E. coli* strain using the oligonucleotides primers DMAR544 and DMAR545 (Table 1). PCR was performed with 30 cycles of 30 sec at 94° C., 30 sec at 51° C. and 1 min 20 sec at 72° C. and a final elongation period of 7 min at 72° C. The PCR products were size fractionated in 1% agarose gels and were visualized by ethidium bromide staining. The results of these PCR amplifications are presented in Table 2. The analysis of the amplification products revealed that BVH-MC2 (SEQ ID NO: 1) gene was present in the genome of all of the 4 *M. catarrhalis* strains tested. No such product was detected when the control *E. coli* DNA was submitted to identical PCR amplifications with these oligonucleotide primers.

Sequencing of additional BVH-MC2 genes from other strains confirmed the high level of molecular conservation of this gene among *M. catarrhalis* strains. The respective coding region of *M. catarrhalis* BVH-MC2 gene from strains ETSU 658 (SEQ ID NO: 3), ETSU T-25 (SEQ ID NO: 5), and M-12 (SEQ ID NO: 7) were amplified by PCR using the oligonucleotide primers DMAR544 and DMAR545 as described above. PCR products were purified from agarose gel using a QIAquick gel extraction kit from QIAgen following the manufacturer's instructions (Chatsworth, Calif.) and the DNA insert were sequenced (Taq Dye Deoxy Terminator Cycle Sequencing kit, ABI, Foster City, Calif.). The total sequence could be obtained in the same manner as in Example 1. The predicted amino acid sequences from strains ETSU C-2 (SEQ ID NO: 2), ETSU 658 (SEQ ID NO: 4), ETSU T-25 (SEQ ID NO: 6), and M-12 (SEQ ID NO: 8) were respectively presented in the following FIGS. 2, 4, 6, and 8. The FIGS. 15 and 16 respectively depict the consensus nucleotide and predicted amino acid sequences established for *M. catarrhalis* BVH-MC2. Pairwise comparison of the BVH-MC2 predicted polypeptide sequences revealed 100% identity. This latter result clearly demonstrates the high level of molecular conservation of BVH-MC2 polypeptides among *M. catarrhalis* isolates.

TABLE 2

Identification of *M. catarrhalis* genes by PCR amplification.

| Strain Identification | Identification by PCR amplification of | | | |
|---|---|---|---|---|
| | BVH-MC2 | BVH-MC3 | BVH-MC4 | BVH-MC5 |
| ETSU C-2 | + | + | + | + |
| ETSU 658 | + | + | + | + |
| ETSU T-25 | + | + | + | + |
| M-12 | + | + | + | + |
| *E. coli* | − | − | − | − |

EXAMPLE 2

This example illustrates the cloning and molecular characteristics of BVH-MC3 gene and corresponding polypeptide.

The coding region of *M. catarrhalis* BVH-MC3 (SEQ ID NO: 9) gene was amplified by PCR (DNA Thermal Cycler GeneAmp PCR system 2400 Perkin Elmer, San Jose, Calif.) from genomic DNA of *M. catarrhalis* strain ETSU C-2 using the following oligos that contained base extensions for the addition of restriction sites NdeI (CATATG) and XhoI (CTCGAG): DMARS92 and DMAR593, which are presented in Table 1. The methods used for cloning BVH-MC3 into an expression vector and sequencing are similar to the methods described in Example 1.

It was determined that the open reading frame (ORF) which codes for BVH-MC3 contains 1656-bp and encodes a 551 amino acid residues polypeptide with a predicted pI of 4.68 and a predicted molecular mass of 58910.13 Da. Analysis of the predicted amino acid residues sequence (SEQ ID NO: 10) using the Spscan software (Wisconsin Sequence Analysis Package; Genetics Computer Group) suggested the existence of a 46 amino acid residues signal peptide (MSLINKLNER ITPHVLTSIKINQDGDNADKSNLLTAFYTIFAGRLSN) (SEQ ID NO:32), which ends with a cleavage site located between an asparagine and a glutamic acid residues.

The BVH-MC3 gene was shown to be present after PCR amplification using the oligonucleotide primers DMAR592 and DMAR593 in the 4 *M. catarrhalis* strains tested (Table 2). The methods used for PCR amplification of the BVH-MC3 gene were similar to the methods presented in Example 1. No such product was detected when the control *E. coli* DNA was submitted to identical PCR amplification with these oligonucleotide primers.

EXAMPLE 3

This example illustrates the cloning and molecular characteristics of BVH-MC4 gene and corresponding polypeptide.

The coding region of *M. catarrhalis* BVH-MC4 (SEQ ID NO: 11) gene was amplified by PCR (DNA Thermal Cycler GeneAmp PCR system 2400 Perkin Elmer, San Jose, Calif.) from genomic DNA of *M. catarrhalis* strain ETSU C-2 using the following oligos that contained base extensions for the addition of restriction sites NdeI (CATATG) and XhoI (CTCGAG): RIOS71 and RIOS72, which are presented in Table 1. The methods used for cloning BVH-MC4 into an expression vector and sequencing are similar to the methods described in Example 1.

It was determined that the open reading frame (ORF) which codes for BVH-MC4 contains 1251-bp and encodes a 416 amino acid residues polypeptide with a predicted pI of 4.84 and a predicted molecular mass of 46125.11 Da. Analysis of the predicted amino acid residues sequence (SEQ ID NO: 12) using the Spscan software (Wisconsin Sequence Analysis Package; Genetics Computer Group) suggested the existence of a 42 amino acid residues signal peptide (MDTKHIQQNWLLPDGVADVLFTDAQKQESL-RDALLFVLTAHG) (SEQ ID SEQ:33), which ends with a cleavage site located between a glycine and a tyrosine residues.

The BVH-MC4 gene was shown to be present after PCR amplification using the oligonucleotide primers RIOS71 and RIOS72 in the 4 *M. catarrhalis* strains tested (Table 2). The methods used for PCR amplification of the BVH-MC4 gene were similar to the methods presented in Example 1. No such product was detected when the control *E. coli* DNA was submitted to identical PCR amplification with these oligonucleotide primers.

EXAMPLE 4

This example illustrates the cloning and molecular characteristics of BVH-MC5 gene and corresponding polypeptide.

The coding region of *M. catarrhalis* BVH-MCS (SEQ ID NO: 13) gene was amplified by PCR (DNA Thermal Cycler GeneAmp PCR system 2400 Perkin Elmer, San Jose, Calif.) from genomic DNA of *M. catarrhalis* strain ETSU C-2 using the following oligos that contained base extensions for the addition of restriction sites NdeI (CATATG) and XhoI (CTCGAG): RIOS59 and RIOS60, which are presented in Table 1. The methods used for cloning BVH-MC5 into an expression vector and sequencing are similar to the methods described in Example 1.

It was determined that the open reading frame (ORF) which codes for BVH-MC5 contains 639-bp and encodes a 212 amino acid residues polypeptide with a predicted pI of 7.45 and a predicted molecular mass of 24020.08 Da. Analysis of the predicted amino acid residues sequence (SEQ ID NO: 14) using the Spscan software (Wisconsin Sequence Analysis Package; Genetics Computer Group) suggested the existence of a 60 amino acid residues signal peptide (MNNFVYQLQSFWYELNQVNRHTIAQSP-KYIQLTVLGLIVMIIGIFGWLLAIL PTIQKLNA) (SEQ ID NO:34), which ends with a cleavage site located between two alanine residues.

The BVH-MC5 gene was shown to be present after PCR amplification using the oligonucleotide primers RIOS59 and RIOS60 in the 4 *M. catarrhalis* strains tested (Table 2). The methods used for PCR amplification of the BVH-MC5 gene were similar to the methods presented in Example 1. No such product was detected when the control *E. coli* DNA was submitted to identical PCR amplification with these oligonucleotide primers.

EXAMPLE 5

This example illustrates the cloning of *M. catarrhalis* genes in CMV plasmid pCMV-GH.

The DNA coding regions of a *M. catarrhalis* polypeptides were inserted in phase downstream of a human growth hormone (hGH) gene which was under the transcriptional control of the cytomegalovirus (CMV) promotor in the plasmid vector pCMV-GH (Tang et al., Nature, 1992, 356:152). The CMV promotor is non-functional plasmid in *E. coli* cells but active upon administration of the plasmid in eukaryotic cells. The vector also incorporated the ampicillin resistance gene.

The coding regions of BVH-MC2 (SEQ ID NO: 1), BVH-MC3 (SEQ ID NO: 9), BVH-MC4 (SEQ ID NO: 11), and BVH-MC5 (SEQ ID NO: 13) genes without their leader peptide regions were amplified by PCR (DNA Thermal Cycler GeneAmp® PCR system 2400 Perkin Elmer, San Jose, Calif.) from genomic DNA of *M. catarrhalis* strain ETSU C-2 using oligonucleotide primers that contained base extensions for the addition of restriction sites BamHI (GGATCC), BglII (AGATCT), SalI (GTCGAC), or HindIII (AAGCTT) which are described in Table 1. The PCR products were purified from agarose gel using a QIA® quick gel extraction kit from QIAgen® (Chatsworth, Calif.), digested with restriction enzymes (Amersham Pharmacia Biotech, Inc, Baie d'Urfe, Canada). The pCMV-GH vector (Laboratory of Dr. Stephen A. Johnston, Department of Biochemistry, The University of Texas, Dallas, Tex.) was digested with BamHI, BglII, SalI, or HindIII and purified from agarose gel using the QIA® quick gel extraction kit from QIAgen® (Chatsworth, Calif.). The digested DNA fragments were ligated to the digested pCMV-GH vector to create the hGH-BVH-MC2, hGH-BVH-MC3, hGH-BVH-MC4, and hGH-BVH-MC5 fusion polypeptides under the control of the CMV promoter. The ligated products were transformed into *E. coli* strain DH5 α [φ80dlacZΔM15 Δ(lacZYA-argF)U169 endA1 recA1 hsdR17($r_K$-$m_K$+) deoR thi-1 supE44 $\lambda^-$gyrA96 relA1] (Gibco BRL, Gaithersburg, Md.) according to the method of Simanis (Hanahan, D. DNA Cloning, 1985, D.M. Glover (ed), pp. 109-135). The recombinant pCMV plasmids were purified using a QIAgen® kit (Chatsworth, Calif.) and the nucleotides sequence of the DNA inserts were verified by DNA sequencing.

EXAMPLE 6

This example illustrates the use of DNA to elicit an immune response to *M. catarrhalis* polypeptide antigens.

A group of 8 female BALB/c mice (Charles River, St-Constant, Québec, Canada) are immunized by intramuscular injection of 100 μl three times at two- or three-week intervals with 50 μg of recombinant pCMV-GH encoding BVH-MC2 (SEQ ID NO: 1), BVH-MC3 (SEQ ID NO: 9), BVH-MC4 (SEQ ID NO: 11), and BVH-MC5 (SEQ ID NO: 13) genes in presence of 50 μg of granulocyte-macrophage colony-stimulating factor (GM-CSF)-expressing plasmid pCMV-GH-GM-CSF (Laboratory of Dr. Stephen A. Johnston, Department of Biochemistry, The University of Texas, Dallas, Tex.). As control, a group of mice are injected with 50 μg of pCMV-GH in the presence of 50 μg of pCMV-GH-GM-CSF. Blood samples are collected from the orbital sinus prior to each immunization and seven days following the third injection and serum antibody responses are determined by ELISA using the corresponding His-Tag labeled *M. catarrhalis* recombinant polypeptides as coating antigen. The production and purification of these His-tagged labeled *M. catarrhalis* recombinant polypeptides are presented in Example 7.

EXAMPLE 7

This example illustrates the production and purification of *M. catarrhalis* recombinant polypeptides.

The recombinant pET21b(+) plasmid with BVH-MC2 (SEQ ID NO: 1), BVH-MC3 (SEQ ID NO: 9), BVH-MC4 (SEQ ID NO: 11), and BVH-MC5 (SEQ ID NO: 13) genes were used to transform by electroporation (Gene Pulser® II apparatus, BIO-RAD Labs, Mississauga, Canada) *E. coli* strain AD494 (DE3) [Δara-leu7697 ΔlacX74 ΔphoA PvuII phoR ΔmalF3 F'[lac$^+$(lacI$^q$) pro] trxB::Kan (DE3)] (Novagen®, Madison, Wis.). In this strain of *E. coli*, the T7 promotor controlling expression of the recombinant polypeptide is specifically recognized by the T7 RNA polymerase (present on the λDE3 prophage) whose gene is under the control of the lac promotor which is inducible by isopropyl-β-d-thio-galactopyranoside (IPTG). The transformant AD494(DE3)/rpET21b(+) was grown at 370° C. with agitation at 250 rpm in LB broth (peptone 10 g/L, yeast extract 5 g/L, NaCl 10 g/L) containing 100 μg of carbenicillin (Sigma-Aldrich Canada Ltd., Oakville, Canada) per ml until the $A_{600}$ reached a value of 0.5. In order to induce the production of His-tagged *M. catarrhalis* recombinant polypeptides, the cells were incubated for 3 additional hours in the presence of IPTG at a final concentration of 1 mM. Induced cells from a 500 ml culture were pelleted by centrifugation and frozen at −70° C.

The purification of the recombinant polypeptides from the soluble cytoplasmic fraction of IPTG-induced AD494(DE3)/rpET21b(+) was done by affinity chromatography based on the properties of the His.Tag sequence (6 consecutive histidine residues) to bind to divalent cations ($Ni^{2+}$) immobilized on the His.Bind metal chelation resin. Briefly, the pelleted cells obtained from a 500 mL culture induced with IPTG was resuspended in lysis buffer (20 mM Tris, 500 mM NaCl, 10 mM imidazole, pH 7.9) containing 1 mM PMSF, sonicated and centrifuged at 12,000 X g for 20 mm to remove debris. The supernatant was deposited on a Ni-NTA agarose column (Qiagen®, Mississauga, Ontario, Canada). The His-tagged labeled *M. catarrhalis* recombinant polypeptides were eluted with 250 mM imidazole-500 mM NaCl-20 mM Tris pH 7.9. The removal of the salt and imidazole from the sample was done by dialysis against PBS at 420 C. The quantities of recombinant polypeptides obtained from the soluble fraction of *E. coli* were estimated by MicroBCA (Pierce, Rockford, Ill.).

EXAMPLE 8

This example illustrates the reactivity of the His-tagged *M. catarrhalis* recombinant polypeptides with human palatine tonsils and sera collected from mice after immunization with *M. catarrhalis* antigenic preparations.

As shown in Table 3, BVH-MC2, BVH-MC3, and BVH-MC4 His-tagged recombinant polypeptides were recognized in immunoblots by the antibodies present in the human palatine tonsils. It indicates that humans, which are normally in contact with *M. catarrhalis* do develop antibodies that are specific to these polypeptides. These particular human antibodies might be implicated in the protection against *M. catarrhalis* infection. In addition, immunoblots also revealed that sera collected from mice immunized with *M. catarrhalis* antigenic preparation enriched membrane polypeptides which induced significant lung clearance in a mouse model also developed antibodies that recognized BVH-MC2 His-tagged recombinant polypeptides. These results indicate that this polypeptide was present in *M. catarrhalis* antigenic preparation that protected mice against infection and that it induced antibodies that reacted with the corresponding BVH-MC2 His-tagged recombinant polypeptide.

TABLE 3

Reactivity in immunoblots of human palatine tonsils and sera collected from mice after immunization with *M. catarrhalis* antigenic preparations with *M. catarrhalis* His-tagged fusion recombinant polypeptides.

| Purified recombinant polypeptide I.D.[1] | Apparent molecular weight (kDa)[2] | Reactivity in immunoblots with | |
|---|---|---|---|
| | | Human palatine tonsils[3] | Mouse sera[4] |
| BVH-MC2 | 50 | + | − |
| BVH-MC3 | 70 | + | + |
| BVH-MC4 | 40 | + | − |
| BVH-MC5 | 20 | − | − |

[1]His-tagged recombinant polypeptides produced and purified as described in Example 7 were used to perform the immunoblots.
[2]Molecular weight of the His-tagged recombinant polypeptide was estimated after SDS-PAGE.
[3]Human palatine tonsils were undiluted to perform the immunoblots.
[4]Mouse sera collected after immunization with *M. catarrhalis* antigenic preparations enriched membrane polypeptides were pooled and diluted 1/500 to perform the immunoblots. These mice were protected against a *M. catarrhalis* challenge.

EXAMPLE 9

This example illustrates the accessibility to antibodies of the BVH-MC2, BVH-MC3, BVH-MC4, and BVH-MC5 polypeptides at the surface of *M. catarrhalis* strain.

Bacteria were grown in Brain Heart Infusion (BHI) broth containing 0.25% dextrose at 37° C. in a 8% $CO_2$ atmosphere to give an $OD_{490\ nm}$ of 0.650 (~$10^8$ CFU/ml). Dilutions of anti-BVH-MC2, anti-BVH-MC3, anti-BVH-MC4, anti-BVH-MC5, or control sera were then added and allowed to bind to the cells, which were incubated for 2 h at 4° C. with rotation. Samples were washed 4 times in blocking buffer [phosphate-buffered saline (PBS) containing 2% bovine serum albumin (BSA)], and then 1 ml of goat fluorescein (FITC)-conjugated anti-mouse IgG Fc (gamma) fragment specific diluted in blocking buffer was added. After an additional incubation of 60 min at room temperature with rotation in the dark, samples were washed 4 times in blocking buffer and fixed with 0.25% formaldehyde in PBS buffer for 18 h at 4° C. Cells were washed 2 times in PBS buffer and resuspended in 0.5 ml of PBS buffer. Cells were kept in the dark at 4° C. until analyzed by flow cytometry (Epics® XL; Beckman Coulter, Inc.). Flow cytometric analysis revealed that BVH-MC2-, BVH-MC3-, BVH-MC4-, and BVH-MC5-specific antibodies efficiently recognized their corresponding surface exposed epitopes on the homologous (ETSU C-2) *M. catarrhalis* strain tested (Table 4). It was determined that more than 70% of the 10,000 *Moraxella* cells analyzed were labeled with the antibodies present in the specific sera. These observations clearly demonstrate that these polypeptides are accessible at the surface where they can be easily recognized by antibodies. Anti-*M. catarrhalis* antibodies were shown to play an important role in the protection against *M. catarrhalis* infection.

TABLE 4

Evaluation of the attachment of BVH-MC2-, BVH-MC3-, BVH-MC4-, and BVH-MC5-specific antibodies at the surface of intact cells of *M. catarrhalis* strain ETSU-C2.

| Serum Identification | Fluorescence Index[2] | % of labeled cells[3] |
|---|---|---|
| Pool of BVH-MC2-specific sera[1] | 3.6 | 72.8 |
| Pool of BVH-MC3-specific sera | 7.5 | 82.8 |
| Pool of BVH-MC4-specific sera | 10.9 | 92.4 |
| Pool of BVH-MC5-specific sera | 6.7 | 77.4 |
| Pool of negative control sera[4] | 1 | 7.4 |
| Positive control serum[5] | 43.8 | 98.7 |

[1]The mice were injected subcutaneously five times at two-week intervals with 20 μg of purified recombinant polypeptides mixed with 10 μg of QuilA ™ (an adjuvant containing saponins from the bark of *Quillaja saponaria*) adjuvant (Cedarlane Laboratories, Hornby, Canada). The sera were diluted 1/50.
[2]The fluorescence index was calculated as the median fluorescence value obtained after labeling the cells with an immune serum divided by the fluorescence value obtained for a control mouse serum. A fluorescence value of 1 indicated that there was no binding of antibodies at the surface of intact *Moraxella* cells.
[3]% of labeled cells out of the 10,000 cells analyzed.
[4]Sera collected from unimmunized or sham-immunized mice were pooled, diluted 1/50, and used as negative controls for this assay.
[5]Serum obtained from a mouse immunized with 20 μg of purified outer membrane polypeptides was diluted 1/1000 and was used as a positive control for the assay.

EXAMPLE 10

This example illustrates the bactericidal activities of anti-BVH-MC2 mouse sera.

Bacteria were plated on chocolate agar plate and incubated at 37° C. in a 8% $CO_2$ atmosphere for 18 h. Bacterial cells were then resuspended in bacteriolysis buffer [10% Hanks' Balanced Salt Solution (HBSS) and 1% hydrolyzed casein, pH 7.3] to an $OD_{490nm}$ of 0.25 and diluted to $8\times10^4$ CFU/ml. The bactericidal assay was performed by mixing 25 μl of the bacterial suspension with 50 μl of diluted heat-inactivated test serum and 15 μl of HBSS and incubating for 15 min at 37° C., 8% $CO_2$ with agitation (200 rpm). The rabbit complement-containing serum was then added to a final concentration of 10%, and the mixture was incubated for an additional 60 min at 37° C., 8% $CO_2$ with agitation (200 rpm) At the end of the incubation period, the number of viable bacteria was determined by plating 10 μl of the assay mixture on chocolate agar plate. The plates were incubated at 37° C. in an 8% $CO_2$ atmosphere for 18-24 h. The control consisted of bacteria incubated with heat-inactivated sera collected from mice before immunization and rabbit complement.

The % of lysis was determined by the following mathematical formula:

$$100 - \left[\frac{A}{B} \times 100\right]$$

A=CFU obtained when the bacteria were incubated with immune sera
B=CFU obtained with pre-bleed sera The *M. catarrhalis* strain ETSU 658 was used to evaluate the bactericidal activity of the sera. Percentage of lysis of 71.3 was determined for mouse sera collected after immunization with purified recombinant BVH-MC2 polypeptide (SEQ ID NO: 2) (Table 5).

TABLE 5

Evaluation of the bactericidal activities of anti-BVH-MC2 mouse sera.

| Identification | Bactericidal titer | % of lysis |
|---|---|---|
| Pool of BVH-MC2-specific sera[1] | 1/35 | 71.3 |
| Positive control serum[2] | 1/35 | 92.7 |

[1]The mice were injected subcutaneously five times at two-week intervals with 20 µg of purified recombinant polypeptides mixed with 10 µg of QuilA ™ adjuvant (Cedarlane Laboratories, Hornby, Canada).
[2]Serum obtained from a mouse immunized with 20 µg of purified outer membrane polypeptides was diluted 1/35 and was used as a positive control for the assay.

EXAMPLE 11

This example illustrates the bactericidal activities of anti-BVH-MC3 mouse sera.

Bacteria were plated on chocolate agar plates and incubated at 37° C. in a 8% $CO_2$ atmosphere for 18 h. Bacterial cells were then resuspended in bacteriolysis buffer [10% Hanks' Balanced Salt Solution (HBSS) and 1% hydrolyzed casein, pH 7.3] to an $OD_{490nm}$ of 0.25 and diluted to $8 \times 10^4$ CFU/ml. The bactericidal assay was performed by mixing 25 µl of the bacterial suspension with 50 µl of diluted heat-inactivated test serum and 15 µl of HBSS and incubating for 15 min at 37° C., 8% $CO_2$ with agitation (200 rpm). The rabbit complement-containing serum was then added to a final concentration of 10%, and the mixture was incubated for an additional 60 min at 37° C., 8% $CO_2$ with agitation (200 rpm) At the end of the incubation period, the number of viable bacteria was determined by plating 10 µl of the assay mixture on chocolate agar plate. The plates were incubated at 37° C. in an 8% $CO_2$ atmosphere for 18-24 h. The control consisted of bacteria incubated with heat-inactivated sera collected from mice before immunization and rabbit complement. The *M. catarrhalis* strain ETSU 658 was used to evaluate the bactericidal activity of the sera. The % of lysis was determined by the following mathematical formula:

$$100 - \left[\frac{A}{B} \times 100\right]$$

A=CFU obtained when the bacteria were incubated with immune sera
B=CFU obtained with pre-bleed sera Bactericidal antibodies were found to be present in the sera collected from the 7 mice that were immunized with the purified recombinant BVH-MC3 polypeptide (Table 6). No bactericidal activity were recorded in the sera collected from control mice (data not shown).

TABLE 6

Evaluation of the bactericidal activity of anti-BVE-MC3 mouse sera.

| Serum identification[1] | % of lysis |
|---|---|
| S1[2] | 33.3 |
| S2 | 67.9 |
| S3 | 89.6 |
| S4 | 66.2 |
| S5 | 78.0 |
| S6 | 90.1 |
| S7 | 37.1 |
| Positive control serum[2] | 77.3 |

[1]The mice S1 to S7 were injected subcutaneously five times at two-week intervals with 20 µg of purified recombinant polypeptide mixed with 10 µg of QuilA ™ adjuvant (Cedarlane Laboratories, Hornby, Canada)
[2]Each mouse serum collected from BVR-MC3 immunized mouse were diluted 1/50.
[3]Serum obtained from a mouse immunized with 20 µg of purified outer membrane polypeptides was diluted 1/50 and was used as a positive control for the assay.

EXAMPLE 12

This example illustrates the protection of mice against *M. catarrhalis* infection induced by immunization with purified recombinant BVH-MC3 polypeptide.

Groups of female BALB/c mice (Charles River) were immunized subcutaneously five times at two-week intervals with 20 µg of affinity purified His-tagged *M. catarrhalis* recombinant BVH-MC3 polypeptide in presence of 10% of QuilA adjuvant (Cedarlane Laboratories Ltd, Hornby, Canada) or, as control, with QuilA adjuvant alone in PBS. Blood samples were collected from the orbital sinus on day 0, 14, 28, 42, and 56 prior to each immunization and 14 days (day 70) following the fifth injection. One week later the mice were challenged intrapulmonary with approximately $1 \times 10^6$ CFU of the *M. catarrhalis* strain ETSU 658. Samples of the *M. catarrhalis* challenge inoculum were plated on chocolate agar plates to determine the CFU and to verify the challenge dose. Mice were killed by an intraperitoneal injection of sodium pentobarbital (Euthanyl™) 5 h after infection. The intact lungs were excised and homogenised in a tissue homogeniser. The lung homogenate were assessed for bacterial clearance by plating the serial dilutions for CFU determination. The % of clearance was determined by the following mathematical formula:

$$100 - \left[\frac{A}{B} \times 100\right]$$

A=CFU obtained with the mice immunized with the BVH-MC3 polypeptide

B=CFU obtained in the control mice

As shown in Table 7, a reduction of 54% in the number of living bacteria were determined for mice immunized with BVH-MC3 polypeptide comparatively to mice in the control group. Thus, immunization with recombinant BVH-MC3 polypeptide promoted rapid clearance of an heterologous strain of *M. catarrhalis* from the lungs of the mice.

TABLE 7

Pulmonary clearance of *Moraxella catarrhalis* by mice immunized with purified recombinant BVH-MC3 polypeptide

| Bacterial recovery from control group (CFU/ml of lung homogenate)[a] | Bacterial recovery from BVH-MC3 group (CFU/ml of lung homogenate)[b] | Bacterial clearance (%)[c] |
| --- | --- | --- |
| $2.4 \times 10^5 \pm 1.9 \times 10^5$ | $1.1 \times 10^5 \pm 7.9 \times 10^4$ | 54 |

[a]Means ± standard deviations for six mice.
[b]Means ± standard deviations for seven mice.
[c]Mice were challenged intrapulmonary with $1 \times 10^6$ CFU of bacteria, and viable bacteria were recovered from lung 5 h after challenge. The % of clearance was calculated with the mathematical formula described above.

The invention claimed is:

1. An isolated polypeptide comprising the amino acid sequence set forth as SEQ ID NO:10, wherein the polypeptide is capable of eliciting immune response in a host *Moraxella catarrhalis* and wherein the isolated polypeptide is capable of eliciting antibodies that specifically binds to a polypeptide consisting of the amino acid sequence set forth as SEQ ID NO:10.

2. The isolated polypeptide of claim 1 from which the signal peptide amino acid sequence set forth as SEQ.ID.NO: 32 is deleted.

3. A pharmaceutical composition that is a vaccine comprising the isolated polypeptide according to either claim 1 or claim 2 and a pharmaceutically acceptable carrier, diluent or adjuvant.

4. A pharmaceutical composition that is a vaccine comprising (a) a pharmaceutically acceptable carrier, diluent or adjuvant and (b) an isolated polypeptide that consists of an amino acid sequence at least 90% identical to the amino acid sequence set forth as SEQ ID NO: 10, wherein the isolated polypeptide is capable of eliciting an immune response in a host against *Moraxella catarrhalis*, and wherein the isolated polypeptide is capable of eliciting antibodies that specifically bind to a polypeptide consisting of the sequence set forth as SEQ ID NO:10.

5. A pharmaceutical composition of that is a vaccine comprising a) a pharmaceutically acceptable carrier, diluent or adjuvant and (b) an isolated polypeptide that comprises an amino acid sequence at least 95% identical to the amino acid sequence set forth as SEQ ID NO:10, wherein the isolated polypeptide is capable of eliciting an immune response in a host against *Moraxella catarrhalis*, and wherein the isolated polypeptide is capable of eliciting antibodies that specifically bind to a polypeptide consisting of the sequence set forth as SEQ ID NO:10.

6. The pharmaceutical composition of claim 5 wherein the isolated polypeptide comprises an amino acid sequence at least 95% identical to the amino acid sequence set forth as SEQ ID NO:10 and from which the signal peptide amino acid sequence set forth as SEQ ID NO:32 is deleted.

7. A kit comprising a polypeptide according to either claim 1 or claim 2 for detection or diagnosis of *Moraxella catarrhalis* infection.

* * * * *

```
                       SEQUENCE LISTING

<160> NUMBER OF SEQ ID NOS: 30

<210> SEQ ID NO 1
<211> LENGTH: 1467
<212> TYPE: DNA
<213> ORGANISM: Moraxella catarrhalis

<400> SEQUENCE: 1
atggacactg acatgaaaca tttaacaaaa catcgcctat cagctgccat cattggcgtt    60
ttattattca ttagcccatc agtgcaagca aatacgacac accatcacac gctaaccagt   120
agcgagctta aacttgctga tgatagtatt attgatagta tcaatcaatt gggtgagctg   180
accgtcaata ttccaaatac acaatatttt caaaccaaca acggtgtgag cgttgctttt   240
acgccattac atgagctgcc tattgtcgat atcagcttgt attttaatgc agggtcagcg   300
tatgaccatc aggttggcaa atcaggcacg gctaacatgg ttgcaaccat gctcacccaa   360
ggaactgaca gcctttctga agatgagttt gttgctgcca aagagcgtct tggcattgat   420
tttaccagta cagcaaataa ggataactta actttatcat taagaagctt gtctgatcaa   480
tcattattaa atcaagccgc cgatttaatg gtcgatgctg tcactcaacc tgcttttgat   540
gataagactc tacaacgcaa caaaaatcag ctcatcacca gttaaaaaca aaaaaagcaa   600
aacccttatc atgtagcttc tgttgcttat catcaagccg tatatgaaaa tcatccttat   660
gcacacgcaa ccacaggcga tgaagatagt attgccaaaa ttgatcgtga tgagctgctt   720
aattttttgc atacttttat taatgcaaat aatgcgacac tggtgattac aggtgatatg   780
accgccgagc aagccaaatc acttgccaac catctgaccg ccaaattacc gacaggcaag   840
tcgtataaaa atacgctgga tttgacaaaa ccagttaagg ctcgtcatat ccatattcct   900
cacaacagta gtcaaaccca aatcatcatc ggtcatccca ccagtaaagt acgcacggac   960
aaagcaggtc gtcaagagtt cagcgatttt tcattaggta atgaaatttt ggcaggtggt  1020
gattttaatg ccagattgat gaaaaccatt cgagagcaaa aaggctacac ttatggcatt  1080
tatggcggta tggaacgcct cagagcaggt ggtaattatg tggttgaatt ttcaaccgat  1140
ggcgataaag cagccgatgc catttagag acgctacaca tcattaatga gtcgctgaat  1200
gaaggcataa cccaagaaga gcttgagttg gtgcgtttgg gcaataaaaa tggttttgcc  1260
aatatttttt caagcaatgc cagtattcat cgtgtcattg gtgctttatt tgttgccgat  1320
tatccaaaag atcatcttaa ccatacgctc aatcgcttgg ataatgccac gataaatagt  1380
```

```
gttaataccg cactgaactt gcgtatcaag cctgatgaat ttatcatcat caccgtgggt    1440
aaaactaagc caaatttgga caaataa                                        1467
```

<210> SEQ ID NO 2
<211> LENGTH: 488
<212> TYPE: PRT
<213> ORGANISM: Moraxella catarrhalis

<400> SEQUENCE: 2

```
Met Asp Thr Asp Met Lys His Leu Thr Lys His Arg Leu Ser Ala Ala
1               5                   10                  15

Ile Ile Gly Val Leu Leu Phe Ile Ser Pro Ser Val Gln Ala Asn Thr
            20                  25                  30

Thr His His His Thr Leu Thr Ser Ser Glu Leu Lys Leu Ala Asp Asp
        35                  40                  45

Ser Ile Ile Asp Ser Ile Asn Gln Leu Gly Glu Leu Thr Val Asn Ile
    50                  55                  60

Pro Asn Thr Gln Tyr Phe Gln Thr Asn Asn Gly Val Ser Val Ala Phe
65                  70                  75                  80

Thr Pro Leu His Glu Leu Pro Ile Val Asp Ile Ser Leu Tyr Phe Asn
                85                  90                  95

Ala Gly Ser Ala Tyr Asp His Gln Val Gly Lys Ser Gly Thr Ala Asn
            100                 105                 110

Met Val Ala Thr Met Leu Thr Gln Gly Thr Asp Ser Leu Ser Glu Asp
        115                 120                 125

Glu Phe Val Ala Ala Lys Glu Arg Leu Gly Ile Asp Phe Thr Ser Thr
    130                 135                 140

Ala Asn Lys Asp Asn Leu Thr Leu Ser Leu Arg Ser Leu Ser Asp Gln
145                 150                 155                 160

Ser Leu Leu Asn Gln Ala Ala Asp Leu Met Val Asp Ala Val Thr Gln
                165                 170                 175

Pro Ala Phe Asp Asp Lys Thr Leu Gln Arg Asn Lys Asn Gln Leu Ile
            180                 185                 190

Thr Ser Leu Lys Gln Lys Lys Gln Asn Pro Tyr His Val Ala Ser Val
        195                 200                 205

Ala Tyr His Gln Ala Val Tyr Glu Asn His Pro Tyr Ala His Ala Thr
    210                 215                 220

Thr Gly Asp Glu Asp Ser Ile Ala Lys Ile Asp Arg Asp Glu Leu Leu
225                 230                 235                 240

Asn Phe Trp His Thr Phe Ile Asn Ala Asn Asn Ala Thr Leu Val Ile
                245                 250                 255

Thr Gly Asp Met Thr Ala Glu Gln Ala Lys Ser Leu Ala Asn His Leu
            260                 265                 270

Thr Ala Lys Leu Pro Thr Gly Lys Ser Tyr Lys Asn Thr Leu Asp Leu
        275                 280                 285

Thr Lys Pro Val Lys Ala Arg His Ile His Ile Pro His Asn Ser Ser
    290                 295                 300

Gln Thr Gln Ile Ile Ile Gly His Pro Thr Ser Lys Val Arg Thr Asp
305                 310                 315                 320

Lys Ala Gly Arg Gln Glu Phe Ser Asp Phe Ser Leu Gly Asn Glu Ile
                325                 330                 335

Leu Ala Gly Gly Asp Phe Asn Ala Arg Leu Met Lys Thr Ile Arg Glu
            340                 345                 350
```

```
Gln Lys Gly Tyr Thr Tyr Gly Ile Tyr Gly Gly Met Glu Arg Leu Arg
        355                 360                 365

Ala Gly Gly Asn Tyr Val Val Glu Phe Ser Thr Asp Gly Asp Lys Ala
    370                 375                 380

Ala Asp Ala Ile Leu Glu Thr Leu His Ile Ile Asn Glu Ser Leu Asn
385                 390                 395                 400

Glu Gly Ile Thr Gln Glu Glu Leu Glu Leu Val Arg Leu Gly Asn Lys
                405                 410                 415

Asn Gly Phe Ala Asn Ile Phe Ser Ser Asn Ala Ser Ile His Arg Val
            420                 425                 430

Ile Gly Ala Leu Phe Val Ala Asp Tyr Pro Lys Asp His Leu Asn His
        435                 440                 445

Thr Leu Asn Arg Leu Asp Asn Ala Thr Ile Asn Ser Val Asn Thr Ala
    450                 455                 460

Leu Asn Leu Arg Ile Lys Pro Asp Glu Phe Ile Ile Thr Val Gly
465                 470                 475                 480

Lys Thr Lys Pro Asn Leu Asp Lys
                485
```

<210> SEQ ID NO 3
<211> LENGTH: 1299
<212> TYPE: DNA
<213> ORGANISM: Moraxella catarrhalis

<400> SEQUENCE: 3

```
gagcttaaac ttgctgatga tagtattatt gatagtatca atcaattggg tgagctgacc      60
gtcaatattc caaatacaca atattttcaa accaacaacg gtgtgagcgt tgcttttacg     120
ccattacatg agctgcctat tgtcgatatc agcttgtatt ttaatgcagg gtcagcgtat     180
gaccatcagg ttggcaaatc aggcacggct aacatggttg caaccatgct cacccaagga     240
actgacagcc tttctgaaga tgagtttgtt gctgccaaag agcgtcttgg cattgatttt     300
accagtacag caaataagga taacttaact ttatcattaa gaagcttgtc tgatcaatca     360
ttattaaatc aagccgccga tttaatggtc gatgctgtca ctcaacctgc ttttgatgat     420
aagactctac aacgcaacaa aaatcagctc atcaccagtt aaaacaaaa aaagcaaaac     480
ccttatcatg tagcttctgt tgcttatcat caagccgtat atgaaaatca tcctatgca     540
cacgcaacca caggcgatga agatagtatt gccaaaattg atcgtgatga gctgcttaat     600
ttttggcata cttttattaa tgcaaataat gcgacactgg tgattacagg tgatatgacc     660
gccgagcaag ccaaatcact tgccaaccat ctgaccgcca aattaccgac aggcaagtcg     720
tataaaaata cgctggattt gacaaaacca gttaaggctc gccatatcca tattcctcac     780
aacagtagtc aaacccaaat catcatcggt cacccccacca gtaaagtacg cacggacaaa     840
gcaggtcgtc aagagttcag cgattttcta ttaggtaatg aaattttggc aggtggtgat     900
tttaatgcca gattgatgaa aaccattcga gagcaaaaag gctacactta tggcatttat     960
ggcggtatgg aacgcctcag agcaggtggt aattatgtgg ttgaattttc aaccgatggc    1020
gataaagcag ccgatgccat tttagagacg ctacacatca ttaatgagtc gctgaatgaa    1080
ggcataaccc aagaagagct tgaattggtg cgtttgggta taaaaatgg ttttgccaat    1140
atttttcaa gcaatgccag tattcatcgt gtcattggtg ctttatttgt tgccgattat    1200
ccaaaagatc atcttaacca tacgctcaat cgcttggata tgccacgat aaatagtgtt    1260
aataccgcac tgaacttgcg tatcaagcct gatgaattt                          1299
```

```
<210> SEQ ID NO 4
<211> LENGTH: 433
<212> TYPE: PRT
<213> ORGANISM: Moraxella catarrhalis

<400> SEQUENCE: 4

Glu Leu Lys Leu Ala Asp Asp Ser Ile Ile Asp Ser Ile Asn Gln Leu
1               5                   10                  15

Gly Glu Leu Thr Val Asn Ile Pro Asn Thr Gln Tyr Phe Gln Thr Asn
            20                  25                  30

Asn Gly Val Ser Val Ala Phe Thr Pro Leu His Glu Leu Pro Ile Val
        35                  40                  45

Asp Ile Ser Leu Tyr Phe Asn Ala Gly Ser Ala Tyr Asp His Gln Val
    50                  55                  60

Gly Lys Ser Gly Thr Ala Asn Met Val Ala Thr Met Leu Thr Gln Gly
65                  70                  75                  80

Thr Asp Ser Leu Ser Glu Asp Glu Phe Val Ala Ala Lys Glu Arg Leu
                85                  90                  95

Gly Ile Asp Phe Thr Ser Thr Ala Asn Lys Asp Asn Leu Thr Leu Ser
            100                 105                 110

Leu Arg Ser Leu Ser Asp Gln Ser Leu Leu Asn Gln Ala Ala Asp Leu
        115                 120                 125

Met Val Asp Ala Val Thr Gln Pro Ala Phe Asp Asp Lys Thr Leu Gln
    130                 135                 140

Arg Asn Lys Asn Gln Leu Ile Thr Ser Leu Lys Gln Lys Lys Gln Asn
145                 150                 155                 160

Pro Tyr His Val Ala Ser Val Ala Tyr His Gln Ala Val Tyr Glu Asn
                165                 170                 175

His Pro Tyr Ala His Ala Thr Thr Gly Asp Glu Asp Ser Ile Ala Lys
            180                 185                 190

Ile Asp Arg Asp Glu Leu Leu Asn Phe Trp His Thr Phe Ile Asn Ala
        195                 200                 205

Asn Asn Ala Thr Leu Val Ile Thr Gly Asp Met Thr Ala Glu Gln Ala
    210                 215                 220

Lys Ser Leu Ala Asn His Leu Thr Ala Lys Leu Pro Thr Gly Lys Ser
225                 230                 235                 240

Tyr Lys Asn Thr Leu Asp Leu Thr Lys Pro Val Lys Ala Arg His Ile
                245                 250                 255

His Ile Pro His Asn Ser Ser Gln Thr Gln Ile Ile Gly His Pro
            260                 265                 270

Thr Ser Lys Val Arg Thr Asp Lys Ala Gly Arg Gln Glu Phe Ser Asp
        275                 280                 285

Phe Ser Leu Gly Asn Glu Ile Leu Ala Gly Gly Asp Phe Asn Ala Arg
    290                 295                 300

Leu Met Lys Thr Ile Arg Glu Gln Lys Gly Tyr Thr Tyr Gly Ile Tyr
305                 310                 315                 320

Gly Gly Met Glu Arg Leu Arg Ala Gly Gly Asn Tyr Val Val Glu Phe
                325                 330                 335

Ser Thr Asp Gly Asp Lys Ala Ala Asp Ala Ile Leu Glu Thr Leu His
            340                 345                 350

Ile Ile Asn Glu Ser Leu Asn Glu Gly Ile Thr Gln Glu Glu Leu Glu
        355                 360                 365

Leu Val Arg Leu Gly Asn Lys Asn Gly Phe Ala Asn Ile Phe Ser Ser
    370                 375                 380
```

```
Asn Ala Ser Ile His Arg Val Ile Gly Ala Leu Phe Val Ala Asp Tyr
385                 390                 395                 400

Pro Lys Asp His Leu Asn His Thr Leu Asn Arg Leu Asp Asn Ala Thr
                405                 410                 415

Ile Asn Ser Val Asn Thr Ala Leu Asn Leu Arg Ile Lys Pro Asp Glu
            420                 425                 430

Phe

<210> SEQ ID NO 5
<211> LENGTH: 1299
<212> TYPE: DNA
<213> ORGANISM: Moraxella catarrhalis

<400> SEQUENCE: 5
gagcttaaac ttgctgatga tagtattatt gatagtatca atcaattggg tgagctgacc      60
gtcaatattc caaatacaca atattttcaa accaacaacg gtgtgagcgt tgcttttacg     120
ccattacatg agctgcctat tgtcgatatc agcttgtatt taatgcaggt cagcgtat      180
gaccatcagg ttggcaaatc aggcacggct aacatggttg caaccatgct cacccaagga     240
actgacagcc tttctgaaga tgagtttgtt gctgccaaag agcgtcttgg cattgatttt     300
accagtacag caaataagga taacttaact ttatcattaa gaagcttgtc tgatcaatca     360
ttattaaatc aagccgccga tttaatggtc gatgctgtca ctcaacctgc ttttgatgat     420
aagactctac aacgcaacaa aaatcagctc atcaccagtt taaacaaaa aaagcaaaac     480
ccttatcatg tagcttctgt tgcttatcat caagccgtat atgaaaatca tccttatgca     540
cacgcaacca caggcgatga agatagtatt gccaaaattg atcgtgatga gctgcttaat     600
ttttggcata cttttattaa tgcaaataat gcgacactgg tgattacagg tgatatgacc     660
gccgagcaag ccaaatcact tgccaaccat ctgaccgcca aattaccgac aggcaagtct     720
tataaaaata cgctggattt gacaaaacca gttaaggctc gccatatcca tattcctcac     780
aacagtagtc aaacccaaat catcatcggt caccccacca gtaaagtacg cacggacaaa     840
gcaggtcgtc aagagttcag cgatttttca ttaggtaatg aaattttggc aggtggtgat     900
tttaatgcca gattgatgaa accattcga gagcaaaaag gctacactta tggcatttat     960
ggcggtatgg aacgcctcag agcaggtggt aattatgtgg ttgaattttc aaccgatggc    1020
gataaagcag ccgatgccat tttagagacg ctacacatca ttaatgagtc gctgaatgaa    1080
ggcataaccc aagaagagct tgagttggtg cgtttgggca ataaaaatgg ttttgccaat    1140
atttttttcaa gcaatgccag tattcatcgt gtcattggtg ctttatttgt tgccgattat    1200
ccaaaagatc atcttaacca tacgctcaat cgcttggata tgccacgat aaatagtgtt    1260
aataccgcac tgaacttgcg tatcaagcct gatgaattt                          1299
```

```
<210> SEQ ID NO 6
<211> LENGTH: 433
<212> TYPE: PRT
<213> ORGANISM: Moraxella catarrhalis

<400> SEQUENCE: 6

Glu Leu Lys Leu Ala Asp Asp Ser Ile Ile Asp Ser Ile Asn Gln Leu
1               5                   10                  15

Gly Glu Leu Thr Val Asn Ile Pro Asn Thr Gln Tyr Phe Gln Thr Asn
            20                  25                  30

Asn Gly Val Ser Val Ala Phe Thr Pro Leu His Glu Leu Pro Ile Val
```

-continued

```
                35                  40                  45
Asp Ile Ser Leu Tyr Phe Asn Ala Gly Ser Ala Tyr Asp His Gln Val
 50                  55                  60
Gly Lys Ser Gly Thr Ala Asn Met Val Ala Thr Met Leu Thr Gln Gly
 65                  70                  75                  80
Thr Asp Ser Leu Ser Glu Asp Phe Val Ala Ala Lys Glu Arg Leu
                 85                  90                  95
Gly Ile Asp Phe Thr Ser Thr Ala Asn Lys Asp Asn Leu Thr Leu Ser
                100                 105                 110
Leu Arg Ser Leu Ser Asp Gln Ser Leu Leu Asn Gln Ala Ala Asp Leu
                115                 120                 125
Met Val Asp Ala Val Thr Gln Pro Ala Phe Asp Asp Lys Thr Leu Gln
130                 135                 140
Arg Asn Lys Asn Gln Leu Ile Thr Ser Leu Lys Gln Lys Gln Asn
145                 150                 155                 160
Pro Tyr His Val Ala Ser Val Ala Tyr His Gln Ala Val Tyr Glu Asn
                165                 170                 175
His Pro Tyr Ala His Ala Thr Thr Gly Asp Glu Asp Ser Ile Ala Lys
                180                 185                 190
Ile Asp Arg Asp Glu Leu Leu Asn Phe Trp His Thr Phe Ile Asn Ala
                195                 200                 205
Asn Asn Ala Thr Leu Val Ile Thr Gly Asp Met Thr Ala Glu Gln Ala
210                 215                 220
Lys Ser Leu Ala Asn His Leu Thr Ala Lys Leu Pro Thr Gly Lys Ser
225                 230                 235                 240
Tyr Lys Asn Thr Leu Asp Leu Thr Lys Pro Val Lys Ala Arg His Ile
                245                 250                 255
His Ile Pro His Asn Ser Ser Gln Thr Gln Ile Ile Gly His Pro
                260                 265                 270
Thr Ser Lys Val Arg Thr Asp Lys Ala Gly Arg Gln Glu Phe Ser Asp
                275                 280                 285
Phe Ser Leu Gly Asn Glu Ile Leu Ala Gly Gly Asp Phe Asn Ala Arg
290                 295                 300
Leu Met Lys Thr Ile Arg Glu Gln Lys Gly Tyr Thr Tyr Gly Ile Tyr
305                 310                 315                 320
Gly Gly Met Glu Arg Leu Arg Ala Gly Gly Asn Tyr Val Val Glu Phe
                325                 330                 335
Ser Thr Asp Gly Asp Lys Ala Ala Asp Ala Ile Leu Glu Thr Leu His
                340                 345                 350
Ile Ile Asn Glu Ser Leu Asn Glu Gly Ile Thr Gln Glu Glu Leu Glu
                355                 360                 365
Leu Val Arg Leu Gly Asn Lys Asn Gly Phe Ala Asn Ile Phe Ser Ser
                370                 375                 380
Asn Ala Ser Ile His Arg Val Ile Gly Ala Leu Phe Val Ala Asp Tyr
385                 390                 395                 400
Pro Lys Asp His Leu Asn His Thr Leu Asn Arg Leu Asp Asn Ala Thr
                405                 410                 415
Ile Asn Ser Val Asn Thr Ala Leu Asn Leu Arg Ile Lys Pro Asp Glu
                420                 425                 430
Phe

<210> SEQ ID NO 7
<211> LENGTH: 1299
```

-continued

```
<212> TYPE: DNA
<213> ORGANISM: Moraxella catarrhalis

<400> SEQUENCE: 7
gagcttaaac ttgctgatga tagtattatt gatagtatca atcaattggg tgagctgacc      60
gtcaatattc caaatacaca atattttcaa accaacaacg gtgtgagcgt tgcttttacg     120
ccattacatg agctgcctat tgtcgatatc agcttgtatt ttaatgcagg gtcagcgtat     180
gaccatcagg ttggcaaatc aggcacggct aacatggttg caaccatgct cacccaagga     240
actgacagcc tttctgaaga tgagtttgtt gctgccaaag agcgtcttgg cattgatttt     300
accagtacag caaataagga taacttaact ttatcattaa gaagcttgtc tgatcaatca     360
ttattaaatc aagccgccga tttaatggtc gatgctgtca ctcaacctgc ttttgatgat     420
aagactctac aacgcaacaa aaatcagctc atcaccagtt aaaacaaaa aaagcaaaac      480 ccttatcatg tagcttctgt tgcttatcat caagccgtat atgaaaatca tccttatgca     540
cacgcaacca caggcgatga agatagtatt gccaaaattg atcgtgatga gctgcttaat     600
ttttggcata cttttattaa tgcaaataat gcgacactgg tgattacagg tgatatgacc     660
gccgagcaag ccaaatcact tgccaaccat ctgaccgcca aattaccgac aggcaagtcg     720
tataaaaata cgctggattt gacaaaacca gttaaggctc gccatatcca tattcctcac     780
aacagtagtc aaacccaaat catcatcggt caccccacca gtaaagtacg cacggacaaa     840
gcaggtcgtc aagagttcag cgattttttca ttaggtaatg aaattttggc aggtggtgat     900
tttaatgcca gattgatgaa aaccattcga gagcaaaaag gctacactta tggcatttat     960
ggcggtatgg aacgcctcag agcaggtggt aattatgtgg ttgaattttc aaccgatggc    1020
gataaagcag ccgatgccat tttagagacg ctacacatca ttaatgagtc gctgaatgaa    1080
ggcataaccc aagaagagct tgaattggtg cgtttgggta taaaaatgg tttttgccaat    1140 attttttcaa gcaatgccag tattcatcgt gtcattggtg ctttatttgt tgccgattat    1200
ccaaaagacc atcttaacca tacgctcaat cgcttggata tgccacgat aaatagtgtt     1260 aataccgcac tgaacttgcg tatcaagcct gatgaattt                          1299

<210> SEQ ID NO 8
<211> LENGTH: 433
<212> TYPE: PRT
<213> ORGANISM: Moraxella catarrhalis

<400> SEQUENCE: 8

Glu Leu Lys Leu Ala Asp Asp Ser Ile Ile Asp Ser Ile Asn Gln Leu
1               5                  10                  15

Gly Glu Leu Thr Val Asn Ile Pro Asn Thr Gln Tyr Phe Gln Thr Asn
            20                  25                  30

Asn Gly Val Ser Val Ala Phe Thr Pro Leu His Glu Leu Pro Ile Val
        35                  40                  45

Asp Ile Ser Leu Tyr Phe Asn Ala Gly Ser Ala Tyr Asp His Gln Val
    50                  55                  60

Gly Lys Ser Gly Thr Ala Asn Met Val Ala Thr Met Leu Thr Gln Gly
65                  70                  75                  80

Thr Asp Ser Leu Ser Glu Asp Glu Phe Val Ala Ala Lys Glu Arg Leu
                85                  90                  95

Gly Ile Asp Phe Thr Ser Thr Ala Asn Lys Asp Asn Leu Thr Leu Ser
            100                 105                 110

Leu Arg Ser Leu Ser Asp Gln Ser Leu Leu Asn Gln Ala Ala Asp Leu
```

-continued

```
                115                 120                 125
Met Val Asp Ala Val Thr Gln Pro Ala Phe Asp Asp Lys Thr Leu Gln
        130                 135                 140

Arg Asn Lys Asn Gln Leu Ile Thr Ser Leu Lys Gln Lys Lys Gln Asn
145                 150                 155                 160

Pro Tyr His Val Ala Ser Val Ala Tyr His Gln Ala Val Tyr Glu Asn
                165                 170                 175

His Pro Tyr Ala His Ala Thr Thr Gly Asp Glu Asp Ser Ile Ala Lys
            180                 185                 190

Ile Asp Arg Asp Glu Leu Leu Asn Phe Trp His Thr Phe Ile Asn Ala
        195                 200                 205

Asn Asn Ala Thr Leu Val Ile Thr Gly Asp Met Thr Ala Glu Gln Ala
210                 215                 220

Lys Ser Leu Ala Asn His Leu Thr Ala Lys Leu Pro Thr Gly Lys Ser
225                 230                 235                 240

Tyr Lys Asn Thr Leu Asp Leu Thr Lys Pro Val Lys Ala Arg His Ile
                245                 250                 255

His Ile Pro His Asn Ser Ser Gln Thr Gln Ile Ile Gly His Pro
            260                 265                 270

Thr Ser Lys Val Arg Thr Asp Lys Ala Gly Arg Gln Glu Phe Ser Asp
        275                 280                 285

Phe Ser Leu Gly Asn Glu Ile Leu Ala Gly Gly Asp Phe Asn Ala Arg
290                 295                 300

Leu Met Lys Thr Ile Arg Glu Gln Lys Gly Tyr Thr Tyr Gly Ile Tyr
305                 310                 315                 320

Gly Gly Met Glu Arg Leu Arg Ala Gly Gly Asn Tyr Val Val Glu Phe
                325                 330                 335

Ser Thr Asp Gly Asp Lys Ala Ala Asp Ala Ile Leu Glu Thr Leu His
            340                 345                 350

Ile Ile Asn Glu Ser Leu Asn Glu Gly Ile Thr Gln Glu Glu Leu Glu
        355                 360                 365

Leu Val Arg Leu Gly Asn Lys Asn Gly Phe Ala Asn Ile Phe Ser Ser
370                 375                 380

Asn Ala Ser Ile His Arg Val Ile Gly Ala Leu Phe Val Ala Asp Tyr
385                 390                 395                 400

Pro Lys Asp His Leu Asn His Thr Leu Asn Arg Leu Asp Asn Ala Thr
                405                 410                 415

Ile Asn Ser Val Asn Thr Ala Leu Asn Leu Arg Ile Lys Pro Asp Glu
            420                 425                 430

Phe
```

<210> SEQ ID NO 9
<211> LENGTH: 1656
<212> TYPE: DNA
<213> ORGANISM: Moraxella catarrhalis

<400> SEQUENCE: 9

```
atgagcttaa ttaataaatt aaatgaacgc attacgccgc atgtcttaac ttcgattaaa      60
aatcaagatg gcgataatgc tgataaatct aatttgttaa ccgcatttta taccattttt     120
gcaggacgct tgagtaatga agatgtgtat cagcgtgcca atgctttgcc tgataatgag     180
cttgagcatg gcatcatct gctcaatgtt gcttttagtg atgttcaac tggtgaagat      240 cagattgctt ctttgagtaa tcaattagcc gatgaatatc atgtttcgcc agtaacggca     300
```

-continued

```
cgcaccgcaa tcgcaacggc agcacctttg gctttggcac gcattaaaga gcaagcaggt    360
gcattatctg taccgtcttt tattcgtact caattggcta agaagaaaaa ccgtttgcca    420
acttgggcgc atactttatt gccagcaggg ctatttgcaa ccgctgccac aaccaccgcc    480
gagcctgtaa cgacagcctc tgctgttgtg aaagagcctg tcaaaccaag tgttgtgaca    540
gaaccagttc atccagctgc ggctaccacc ccagtcaaaa caccaactgc ccagcattac    600
gaaaacaaag aaaaaagtcc ttttctaaaa acgattctac cgattattgg attgattatt    660
tttgcaggct tggcatggct tttgttaaga gcatgtcaag acaaaccaac acctgttgcg    720
gcacctgttg cgacagatac agcacctgtg gtagcggata atgctgtaca ggcagaccca    780
acacaaacag gtgttgccca agcacctgca acgcttagct tgtctgttga tgaaacgggt    840
caagcgttgt actcgcaccg tgctcaggtt ggtagtgaag agcttgcagg tcatatccgt    900
gcagctattg ctcaagtctt tggcgtacaa gatttaacca ttcaaaatac caatgtacat    960
accgctacga tgccagcggc agaatactta ccagcaattt tgggtttgat gaaaggtgta   1020
ccaaattcaa gcgttgtgat tcatgatcat acggtacgct taatgcaac acgccagaa    1080
gatgtagcaa aactggtaga gggtgctaaa aatattctac ccgctgattt tactgtagaa   1140
gcagaacctg aacttgatat taatactgcg gttgccgata gtattgaaac agcgcgtgtt   1200
gctattgttg ctttgggtga tacgttgaa gaaaatgaga tggatatttt aatcaatgca   1260
ttaaataccc aaatcattaa ctttgcttta gactcaaccg aaattcccca agaaaataaa   1320
gaaatcttgg atttggctgc cgaaaaatta aaggcagtgc ctgaaacaac tttgcgtatc   1380
attggtcata cagacactca aggcacacat gagtataatc aagatttatc agaatctcgt   1440
gctgctgctg ttaaagagta tttggtatca aaaggtgttg ctgctgaacg cttgaacact   1500
caaggtgcaa gttttgatta tccagttgca tcaaatgcta ccgaacaagg tcgcttccaa   1560
aaccgtcgta ttgagtttgt actttttccaa gaaggtgaag caattactca gtcggtcat   1620
gctgaagatg caccaacacc tgttgcacaa aactga                           1656
```

<210> SEQ ID NO 10
<211> LENGTH: 551
<212> TYPE: PRT
<213> ORGANISM: Moraxella catarrhalis

<400> SEQUENCE: 10

```
Met Ser Leu Ile Asn Lys Leu Asn Glu Arg Ile Thr Pro His Val Leu
1               5                   10                  15

Thr Ser Ile Lys Asn Gln Asp Gly Asp Asn Ala Asp Lys Ser Asn Leu
            20                  25                  30

Leu Thr Ala Phe Tyr Thr Ile Phe Ala Gly Arg Leu Ser Asn Glu Asp
        35                  40                  45

Val Tyr Gln Arg Ala Asn Ala Leu Pro Asp Asn Glu Leu Glu His Gly
    50                  55                  60

His His Leu Leu Asn Val Ala Phe Ser Asp Val Ser Thr Gly Glu Asp
65                  70                  75                  80

Gln Ile Ala Ser Leu Ser Asn Gln Leu Ala Asp Glu Tyr His Val Ser
                85                  90                  95

Pro Val Thr Ala Arg Thr Ala Ile Ala Thr Ala Pro Leu Ala Leu
            100                 105                 110

Ala Arg Ile Lys Glu Gln Ala Gly Ala Leu Ser Val Pro Ser Phe Ile
        115                 120                 125

Arg Thr Gln Leu Ala Lys Glu Glu Asn Arg Leu Pro Thr Trp Ala His
```

```
            130                 135                 140
Thr Leu Leu Pro Ala Gly Leu Phe Ala Thr Ala Thr Thr Ala
145                 150                 155                 160

Glu Pro Val Thr Thr Ala Ser Ala Val Val Lys Glu Pro Val Lys Pro
                    165                 170                 175

Ser Val Val Thr Glu Pro Val His Pro Ala Ala Thr Thr Pro Val
                180                 185                 190

Lys Thr Pro Thr Ala Gln His Tyr Glu Asn Lys Glu Lys Ser Pro Phe
            195                 200                 205

Leu Lys Thr Ile Leu Pro Ile Ile Gly Leu Ile Ile Phe Ala Gly Leu
210                 215                 220

Ala Trp Leu Leu Leu Arg Ala Cys Gln Asp Lys Pro Thr Pro Val Ala
225                 230                 235                 240

Ala Pro Val Ala Thr Asp Thr Ala Pro Val Val Ala Asp Asn Ala Val
                245                 250                 255

Gln Ala Asp Pro Thr Gln Thr Gly Val Ala Gln Ala Pro Ala Thr Leu
                260                 265                 270

Ser Leu Ser Val Asp Glu Thr Gly Gln Ala Leu Tyr Ser His Arg Ala
            275                 280                 285

Gln Val Gly Ser Glu Glu Leu Ala Gly His Ile Arg Ala Ala Ile Ala
            290                 295                 300

Gln Val Phe Gly Val Gln Asp Leu Thr Ile Gln Asn Thr Asn Val His
305                 310                 315                 320

Thr Ala Thr Met Pro Ala Ala Glu Tyr Leu Pro Ala Ile Leu Gly Leu
                325                 330                 335

Met Lys Gly Val Pro Asn Ser Ser Val Val Ile His Asp His Thr Val
                340                 345                 350

Arg Phe Asn Ala Thr Thr Pro Glu Asp Val Ala Lys Leu Val Glu Gly
            355                 360                 365

Ala Lys Asn Ile Leu Pro Ala Asp Phe Thr Val Glu Ala Glu Pro Glu
            370                 375                 380

Leu Asp Ile Asn Thr Ala Val Ala Asp Ser Ile Glu Thr Ala Arg Val
385                 390                 395                 400

Ala Ile Val Ala Leu Gly Asp Thr Val Glu Glu Asn Glu Met Asp Ile
                405                 410                 415

Leu Ile Asn Ala Leu Asn Thr Gln Ile Ile Asn Phe Ala Leu Asp Ser
                420                 425                 430

Thr Glu Ile Pro Gln Glu Asn Lys Glu Ile Leu Asp Leu Ala Ala Glu
            435                 440                 445

Lys Leu Lys Ala Val Pro Glu Thr Thr Leu Arg Ile Ile Gly His Thr
450                 455                 460

Asp Thr Gln Gly Thr His Glu Tyr Asn Gln Asp Leu Ser Glu Ser Arg
465                 470                 475                 480

Ala Ala Ala Val Lys Glu Tyr Leu Val Ser Lys Gly Val Ala Ala Glu
                485                 490                 495

Arg Leu Asn Thr Gln Gly Ala Ser Phe Asp Tyr Pro Val Ala Ser Asn
            500                 505                 510

Ala Thr Glu Gln Gly Arg Phe Gln Asn Arg Arg Ile Glu Phe Val Leu
            515                 520                 525

Phe Gln Glu Gly Glu Ala Ile Thr Gln Val Gly His Ala Glu Asp Ala
530                 535                 540

Pro Thr Pro Val Ala Gln Asn
545                 550
```

-continued

<210> SEQ ID NO 11
<211> LENGTH: 1251
<212> TYPE: DNA
<213> ORGANISM: Moraxella catarrhalis

<400> SEQUENCE: 11

| | | | | | |
|---|---|---|---|---|---|
| atggatacaa | aacacattca | gcaaaattgg | cttctacctg | atggtgtggc | tgatgtacta | 60 |
| tttaccgatg | ctcaaaaaca | agaaagcctg | cgtgatgcct | tgctatttgt | gctaaccgca | 120 |
| cacggttatc | gcttggtgtc | accaccatta | atagagtata | ccgaaagtct | gctaaataat | 180 |
| gctgacgaag | atctaaaacg | ccaaactttc | aaatttatcg | atcagctcaa | tggtcgtttg | 240 |
| atgggttttgc | gtgccgatat | tacgccacaa | attctacgca | ttgatagcaa | atatggtcaa | 300 |
| ggcatcagcc | gttactgtta | tgttgggcaa | gttgtcaaaa | ccctaccgac | tggtctgttt | 360 |
| gggctgcgta | caccgcttca | attgggtgct | gagattttg | ggatagatga | tatccgtgcc | 420 |
| gagcttgagc | tgattgatct | attggccgca | ttggcagatg | agatcggact | aggccgagag | 480 |
| atgctacatg | tggatattgg | tcatgtcgct | atttttgatc | gcttgtgtca | gttgcatggc | 540 |
| gtttcaaata | aagatgctga | tgagctgatt | ggcatttacc | ataaaaaagc | catgccagaa | 600 |
| cttgccaaat | ggtgccaaaa | tattggcaat | agcctaaaca | gcccaagcga | tgcaaccgat | 660 |
| tttttggtat | tggctaagca | tacattaagc | agtgatcgga | caccaaatgc | cgaggcttta | 720 |
| ttaagtaaac | tgtccgataa | agctcgccaa | gataataaaa | tcatccaagc | ggcaaatgag | 780 |
| cttgctactt | tggcggcaca | tatcagagcg | gtgggtatga | gtgtgagtat | tgatgtgact | 840 |
| gaattgtcag | atatcattta | tcatactggt | gtggtatttta | atgtctattt | gggtaataga | 900 |
| accacacaga | ctcaagcttt | ggtacgaggc | ggtcgctttg | atggtatctc | aactcacagc | 960 |
| gtagcaaggg | gcgcaactgg | ttttagcatg | gatattaatc | gtttgcttga | atttgtagag | 1020 |
| cttgaagaag | atactgtgat | tttggtggat | tatcacgatt | tgcaaaatgc | tgatgcagac | 1080 |
| acaaaagctg | atttggccac | acaaattaaa | accttgcaat | ctgaaggctg | tattgtcatt | 1140 |
| aagcctttga | ctgtagatga | taagcctaac | cagattgatg | tgttttgca | ttgggacacc | 1200 |
| gatcaagata | agccgatttg | ggcggtgcga | ttagttggtg | atgagtacta | a | 1251 |

<210> SEQ ID NO 12
<211> LENGTH: 416
<212> TYPE: PRT
<213> ORGANISM: Moraxella catarrhalis

<400> SEQUENCE: 12

Met Asp Thr Lys His Ile Gln Gln Asn Trp Leu Leu Pro Asp Gly Val
1               5                   10                  15

Ala Asp Val Leu Phe Thr Asp Ala Gln Lys Gln Glu Ser Leu Arg Asp
            20                  25                  30

Ala Leu Leu Phe Val Leu Thr Ala His Gly Tyr Arg Leu Val Ser Pro
        35                  40                  45

Pro Leu Ile Glu Tyr Thr Glu Ser Leu Leu Asn Asn Ala Asp Glu Asp
    50                  55                  60

Leu Lys Arg Gln Thr Phe Lys Phe Ile Asp Gln Leu Asn Gly Arg Leu
65                  70                  75                  80

Met Gly Leu Arg Ala Asp Ile Thr Pro Gln Ile Leu Arg Ile Asp Ser
                85                  90                  95

Lys Tyr Gly Gln Gly Ile Ser Arg Tyr Cys Tyr Val Gly Gln Val Val
            100                 105                 110

Lys Thr Leu Pro Thr Gly Leu Phe Gly Leu Arg Thr Pro Leu Gln Leu
            115                 120                 125

Gly Ala Glu Ile Phe Gly Ile Asp Asp Ile Arg Ala Glu Leu Glu Leu
        130                 135                 140

Ile Asp Leu Leu Ala Ala Leu Ala Asp Glu Ile Gly Leu Gly Arg Glu
145                 150                 155                 160

Met Leu His Val Asp Ile Gly His Val Ala Ile Phe Asp Arg Leu Cys
                165                 170                 175

Gln Leu His Gly Val Ser Asn Lys Asp Ala Asp Glu Leu Ile Gly Ile
            180                 185                 190

Tyr His Lys Lys Ala Met Pro Glu Leu Ala Lys Trp Cys Gln Asn Ile
        195                 200                 205

Gly Asn Ser Leu Asn Ser Pro Ser Asp Ala Thr Asp Phe Leu Val Leu
    210                 215                 220

Ala Lys His Thr Leu Ser Ser Asp Arg Thr Pro Asn Ala Glu Ala Leu
225                 230                 235                 240

Leu Ser Lys Leu Ser Asp Lys Ala Arg Gln Asp Asn Lys Ile Ile Gln
                245                 250                 255

Ala Ala Asn Glu Leu Ala Thr Leu Ala Ala His Ile Arg Ala Val Gly
            260                 265                 270

Met Ser Val Ser Ile Asp Val Thr Glu Leu Ser Gly Tyr His Tyr His
        275                 280                 285

Thr Gly Val Val Phe Asn Val Tyr Leu Gly Asn Arg Thr Thr Gln Thr
    290                 295                 300

Gln Ala Leu Val Arg Gly Gly Arg Phe Asp Gly Ile Ser Thr His Ser
305                 310                 315                 320

Val Ala Arg Gly Ala Thr Gly Phe Ser Met Asp Ile Asn Arg Leu Leu
                325                 330                 335

Glu Phe Val Glu Leu Glu Glu Asp Thr Val Ile Leu Val Asp Tyr His
            340                 345                 350

Asp Leu Gln Asn Ala Asp Ala Asp Thr Lys Ala Asp Leu Ala Thr Gln
        355                 360                 365

Ile Lys Thr Leu Gln Ser Glu Gly Cys Ile Val Ile Lys Pro Leu Thr
    370                 375                 380

Val Asp Asp Lys Pro Asn Gln Ile Asp Gly Val Leu His Trp Asp Thr
385                 390                 395                 400

Asp Gln Asp Lys Pro Ile Trp Ala Val Arg Leu Val Gly Asp Glu Tyr
                405                 410                 415

<210> SEQ ID NO 13
<211> LENGTH: 639
<212> TYPE: DNA
<213> ORGANISM: Moraxella catarrhalis

<400> SEQUENCE: 13 ataataatt tgtgtatca gctacaaagt ttttggtatg agcttaatca ggtcaatcgt      60
cataccattg ctcaatcacc caaatatata cagctgacgg tacttggttt gatcgtgatg    120
atcattggca ttttggctg ctacttgcg attttaccaa ccattcaaaa gcttaatgca    180
gcccaaagtc aagaatctgc cttaattgat gaatttgcca ctaaatatca taagcccag    240 cagtttgacc atctaagcca tcaggtcata caaaaaaata cacaacttga aaatcagctc    300
aatgctctgc cacgcacagc accgatgagc gagattatcg aatgataaaa taccaaagca    360
caagcggtta atgtgcaggt ggtgagtgca tcagttcaag caggtcgtga acaggattat    420

```
tataccgaac gccctatcgc agtgagtgcg acaggggatt atcatgcttt gggtcgatgg      480
ttacttgagt tgtcagaggc taaccatttg ctgacagtgc atgattttga tctgaaggct      540
ggtttgaacc atcagctgat gatgattgct cagatgaaaa cttatcaagc aaacaaacgc      600
ccaaaaccag ttgctcagca ggtgcctgat gttcaatga                            639
```

<210> SEQ ID NO 14
<211> LENGTH: 212
<212> TYPE: PRT
<213> ORGANISM: Moraxella catarrhalis

<400> SEQUENCE: 14

```
Met Asn Asn Phe Val Tyr Gln Leu Gln Ser Phe Trp Tyr Glu Leu Asn
1               5                   10                  15

Gln Val Asn Arg His Thr Ile Ala Gln Ser Pro Lys Tyr Ile Gln Leu
            20                  25                  30

Thr Val Leu Gly Leu Ile Val Met Ile Ile Gly Ile Phe Gly Trp Leu
        35                  40                  45

Leu Ala Ile Leu Pro Thr Ile Gln Lys Leu Asn Ala Ala Gln Ser Gln
    50                  55                  60

Glu Ser Ala Leu Ile Asp Glu Phe Ala Thr Lys Tyr His Lys Ala Gln
65                  70                  75                  80

Gln Phe Asp His Leu Ser His Gln Val Ile Gln Lys Asn Thr Gln Leu
                85                  90                  95

Glu Asn Gln Leu Asn Ala Leu Pro Arg Thr Ala Pro Met Ser Glu Ile
            100                 105                 110

Ile Gly Met Ile Asn Thr Lys Ala Gln Ala Val Asn Val Gln Val Val
        115                 120                 125

Ser Ala Ser Val Gln Ala Gly Arg Glu Gln Asp Tyr Tyr Thr Glu Arg
    130                 135                 140

Pro Ile Ala Val Ser Ala Thr Gly Asp Tyr His Ala Leu Gly Arg Trp
145                 150                 155                 160

Leu Leu Glu Leu Ser Glu Ala Asn His Leu Leu Thr Val His Asp Phe
                165                 170                 175

Asp Leu Lys Ala Gly Leu Asn His Gln Leu Met Met Ile Ala Gln Met
            180                 185                 190

Lys Thr Tyr Gln Ala Asn Lys Arg Pro Lys Pro Val Ala Gln Gln Val
        195                 200                 205

Pro Asp Val Gln
    210
```

<210> SEQ ID NO 15
<211> LENGTH: 35
<212> TYPE: DNA
<213> ORGANISM: Artificial
<220> FEATURE:
<223> OTHER INFORMATION: primer

<400> SEQUENCE: 15

```
catcagtgca tatgaatacg acacaccatc acacg                                35
```

<210> SEQ ID NO 16
<211> LENGTH: 40
<212> TYPE: DNA
<213> ORGANISM: Artificial
<220> FEATURE:
<223> OTHER INFORMATION: primer -continued

<400> SEQUENCE: 16
gagttattct cgagtttgtc caaatttggc ttagttttac                              40

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
tcagtgagat cttgaatacg acacaccatc                                         30

<210> SEQ ID NO 18
<211> LENGTH: 33
<212> TYPE: DNA
<213> ORGANISM: Artificial
<220> FEATURE:
<223> OTHER INFORMATION: primer

<400> SEQUENCE: 18
gatttgagtt gtcgacttat ttgtccaaat ttg                                     33

<210> SEQ ID NO 19
<211> LENGTH: 36
<212> TYPE: DNA
<213> ORGANISM: Artificial
<220> FEATURE:
<223> OTHER INFORMATION: primer

<400> SEQUENCE: 19
cggagtgcca tatgagctta attaataaat taaatg                                  36

<210> SEQ ID NO 20
<211> LENGTH: 31
<212> TYPE: DNA
<213> ORGANISM: Artificial
<220> FEATURE:
<223> OTHER INFORMATION: primer

<400> SEQUENCE: 20
tataactcga ggttttgtgc aacaggtgtt g                                       31

<210> SEQ ID NO 21
<211> LENGTH: 34
<212> TYPE: DNA
<213> ORGANISM: Artificial
<220> FEATURE:
<223> OTHER INFORMATION: primer

<400> SEQUENCE: 21
cgcttgagat cttggaagat gtgtatcagc gtgc                                    34

<210> SEQ ID NO 22
<211> LENGTH: 37
<212> TYPE: DNA
<213> ORGANISM: Artificial
<220> FEATURE:
<223> OTHER INFORMATION: primer

<400> SEQUENCE: 22
caataacaaa gctttcagtt ttgtgcaaca ggtgttg                                 37

<210> SEQ ID NO 23
<211> LENGTH: 33

```
<212> TYPE: DNA
<213> ORGANISM: Artificial
<220> FEATURE:
<223> OTHER INFORMATION: primer

<400> SEQUENCE: 23
aaccgcacat atgtatcgct tggtgtcacc acc                              33

<210> SEQ ID NO 24
<211> LENGTH: 35
<212> TYPE: DNA
<213> ORGANISM: Artificial
<220> FEATURE:
<223> OTHER INFORMATION: primer

<400> SEQUENCE: 24
ggtgactcga ggtactcatc accaactaat cgcac                            35

<210> SEQ ID NO 25
<211> LENGTH: 27
<212> TYPE: DNA
<213> ORGANISM: Artificial
<220> FEATURE:
<223> OTHER INFORMATION: primer

<400> SEQUENCE: 25
gcaggatcct tatcgcttgg tgtcacc                                     27

<210> SEQ ID NO 26
<211> LENGTH: 31
<212> TYPE: DNA
<213> ORGANISM: Artificial
<220> FEATURE:
<223> OTHER INFORMATION: primer

<400> SEQUENCE: 26
atcaatcggg tcgacttagt actcatcacc a                                31

<210> SEQ ID NO 27
<211> LENGTH: 34
<212> TYPE: DNA
<213> ORGANISM: Artificial
<220> FEATURE:
<223> OTHER INFORMATION: primer

<400> SEQUENCE: 27
aaagcttcat atggcccaaa gtcaagaatc tgcc                             34

<210> SEQ ID NO 28
<211> LENGTH: 31
<212> TYPE: DNA
<213> ORGANISM: Artificial
<220> FEATURE:
<223> OTHER INFORMATION: primer

<400> SEQUENCE: 28
cgataactcg agttgaacat caggcacctg c                                31

<210> SEQ ID NO 29
<211> LENGTH: 39
<212> TYPE: DNA
<213> ORGANISM: Artificial
<220> FEATURE:
<223> OTHER INFORMATION: primer

<400> SEQUENCE: 29
```

```
accattcaaa agagatcttg gcccaaagtc aagaatctg                                   39

<210> SEQ ID NO 30
<211> LENGTH: 33
<212> TYPE: DNA
<213> ORGANISM: Artificial
<220> FEATURE:
<223> OTHER INFORMATION: primer

<400> SEQUENCE: 30
gttagaccga gtcgactcat tgaacatcag gca                                         33
```